US007618987B2

(12) United States Patent
Bakshi et al.

(10) Patent No.: US 7,618,987 B2
(45) Date of Patent: Nov. 17, 2009

(54) ACYLATED PIPERIDINE DERIVATIVES AS MELANOCORTIN 4-RECEPTOR AGONISTS

(75) Inventors: Raman K. Bakshi, Edison, NJ (US); James P. Dellureficio, Millington, NJ (US); Ravi P. Nargund, East Brunswick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 238 days.

(21) Appl. No.: 11/632,000

(22) PCT Filed: Jul. 15, 2005

(86) PCT No.: PCT/US2005/025505

§ 371 (c)(1),
(2), (4) Date: Jan. 9, 2007

(87) PCT Pub. No.: WO2006/020277

PCT Pub. Date: Feb. 23, 2006

(65) Prior Publication Data

US 2007/0191433 A1    Aug. 16, 2007

Related U.S. Application Data

(60) Provisional application No. 60/589,089, filed on Jul. 19, 2004.

(51) Int. Cl.
*C07D 401/02* (2006.01)
*A61K 31/454* (2006.01)

(52) U.S. Cl. .................. 514/326; 546/208
(58) Field of Classification Search .......... 546/189, 546/208; 514/326
See application file for complete search history.

(56) References Cited

U.S. PATENT DOCUMENTS

| | | | |
|---|---|---|---|
| 6,294,534 B1 | 9/2001 | Nargund et al. | |
| 6,350,760 B1 | 2/2002 | Bakshi et al. | |
| 6,376,509 B1 | 4/2002 | Bakshi et al. | |
| 6,410,548 B2 | 6/2002 | Nargund et al. | |
| 6,458,790 B2 | 10/2002 | Palucki et al. | |
| 6,472,398 B1 | 10/2002 | Palucki et al. | |
| 6,713,487 B2 | 3/2004 | Yu et al. | |
| 6,818,658 B2 * | 11/2004 | Ujjainwalla et al. | 514/326 |
| 7,015,235 B2 * | 3/2006 | Goulet et al. | 514/330 |
| 2002/0004512 A1 | 1/2002 | Bakshi et al. | |
| 2002/0019523 A1 | 2/2002 | Palucki et al. | |
| 2002/0137664 A1 | 9/2002 | Bakshi et al. | |
| 2003/0092732 A1 | 5/2003 | Yu et al. | |
| 2004/0097546 A1 | 5/2004 | Goulet et al. | |

FOREIGN PATENT DOCUMENTS

| | | |
|---|---|---|
| WO | WO 99/64002 | 12/1999 |
| WO | WO 00/74679 | 12/2000 |
| WO | WO 01/58891 | 8/2001 |
| WO | WO 01/70337 | 9/2001 |
| WO | WO 01/70708 | 9/2001 |
| WO | WO 01/91752 | 12/2001 |
| WO | WO 02/15909 | 2/2002 |
| WO | WO 02/067869 | 9/2002 |
| WO | WO 02/068387 | 9/2002 |
| WO | WO 02/068388 | 9/2002 |
| WO | WO 02/079146 | 10/2002 |
| WO | WO 03/007949 | 1/2003 |
| WO | WO 03/009847 | 2/2003 |
| WO | WO 03/057671 | 7/2003 |
| WO | WO 03/066597 | 8/2003 |
| WO | WO 03/068738 | 8/2003 |
| WO | WO 03/092690 | 11/2003 |
| WO | WO 2004/024720 | 3/2004 |
| WO | WO 2004/037797 | 5/2004 |
| WO | WO 2004/078716 | 6/2004 |
| WO | WO 2004/078717 | 9/2004 |

OTHER PUBLICATIONS

Fischer et. al. "Privileged structure based ligands for melanocortin receptors-Substituted benzylic piperazine derivatives". Bioorganic & Medicinal Chemistry Letters 2005, 15, 4973-4978.*
Hogan et. al. "Mapping the Binding Site of Melanocortin 4 Receptor Agonists: A Hydrophobic Pocket Formed by 13.28(125), 13.32(129), and 17.42(291) Is Critical for Receptor Activation" Journal of Medicinal Chemistry 2006, 49, 911-922.*
Sebhat et. al. "Melanocortin subtype 4 receptor agonists: Structure-activity relationships about the 4-alkyl piperidine core" Bioorganic & Medicinal Chemistry Letters 2007, 17, 5720-5723.*
Guo et. al. "Synthesis and SAR of potent and orally bioavailable tert-butylpyrrolidine archetype derived melanocortin subtype-4 receptor modulators" Bioorganic & Medicinal Chemistry Letters 2008, 18, 3242-3247.*
Poitout et. al. "Identification of a novel series of benzimidazoles as potent and selective antagonists of the human melanocortin-4 receptor" Bioorganic & Medicinal Chemistry Letters 2007, 17, 4464-4470.*

* cited by examiner

*Primary Examiner*—Rita J Desai
*Assistant Examiner*—David K O'Dell
(74) *Attorney, Agent, or Firm*—Eaerbel R. Brown; Catherine D. Fitch

(57) ABSTRACT

Certain novel N-acylated piperidine derivatives are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

6 Claims, No Drawings

ACYLATED PIPERIDINE DERIVATIVES AS MELANOCORTIN 4-RECEPTOR AGONISTS

CROSS-REFERENCE TO RELATED APPLICATIONS

This application is a U.S. National Phase application under 35 U.S.C §317 of PCT Application No. PCT/US2005/025505, filed Jul. 15, 2005, which claims priority under 35 U.S.C. §119 from U.S. Provisional Application No. 60/589,089, filed Jul. 19, 2004.

FIELD OF THE INVENTION

The present invention relates to acylated piperidine derivatives, their synthesis, and their use as melanocortin receptor (MC-R) modulators. More particularly, the compounds of the present invention are selective agonists of the melanocortin-4 receptor (MC-4R) and are thereby useful for the treatment of disorders responsive to the activation of MC-4R, such as obesity, diabetes, male sexual dysfunction, and female sexual dysfunction.

BACKGROUND OF THE INVENTION

The melanocortin 4 receptor is implicated in the control of food intake and energy expenditure, and in modulating erectile function and sexual behavior (Van der Ploeg et al., PNAS, Vol. 99, No. 17, 11381-11386 (2002); Martin et al., European Urology, Vol. 45, Issue 6, 706-713 (2004). Obesity is a major health concern in Western societies. It is estimated that about 97 million adults in the United States are overweight or obese. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancer; osteoarthritis; respiratory complications, such as obstructive sleep apnea; cholelithiasis; gallstones; arterioscelerosis; heart disease; abnormal heart rhythms; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death. Obesity also exacerbates many health problems, both independently and in association with other diseases.

Pro-opiomelanocortin (POMC) derived peptides are known to affect food intake. Five distinct MC-R's have thus far been identified, and these are expressed in different tissues. MC-1R is mainly expressed in melanocytes, and has been found to affect coat color by controlling phaeomelanin to eumelanin conversion through control of tyrosinase. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," *Biochem. Biophys. Res. Commun.*, 245: 90-93 (1998)). MC-5R is expressed in many tissues, including white fat, placenta and exocrine glands, and in the brain. MC-5R knockout mice reveal reduced sebaceous gland lipid production (Chen et al., *Cell*, 91: 789-798 (1997)). A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," *Brain Research*, 80: 302-306 (1998)).

Weight loss drugs that are currently used to treat obesity have limited efficacy. Studies of the weight loss medications orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &:189-98) and phentermine (Douglas, A. et al. (1983) Int. J. Obes. 7:591-5) have demonstrated a limited weight loss of about 5%-10% of body weight for drug compared to placebo. The side effects of these anti-obesity agents further limit their use. Dexfenfluramine was withdrawn from the market because of suspected heart valvulopathy; orlistat is limited by gastrointestinal side effects; the use of topiramate is limited by central nervous system effects; and the use of sibutramine is limited by its cardiovascular side effects which have led to reports of deaths and its withdrawal from the market in Italy.

There is a need for a weight loss treatment with enhanced efficacy and fewer undesirable side effects. The instant invention addresses this problem by providing melanocortin receptor (MC-R) agonists, and in particular selective agonists of the melanocortin-4 receptor (MC-4R), useful in the treatment and prevention of obesity and obesity-related disorders, including diabetes.

Melanocortin receptor involvement in male and female sexual dysfunction has also been reported. Approximately 140 million men worldwide suffer from impotency or erectile dysfunction. Erectile dysfunction or "impotence" denotes the medical condition of inability to achieve penile erection sufficient for successful sexual intercourse. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men with Psychogenic Erectile Dysfunction: Double-Blind, Placebo Controlled Crossover Study," *J. Urol.*, 160: 389-393 (1998); *Fifteenth American Peptide Symposium*, Jun. 14-19, 1997 (Nashville Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate when injected intramuscularly or subcutaneously to males with psychogenic erectile dysfunction. MT-II (PT-14; Erectide®) is a synthetic cyclic heptapeptide, Ac-Nle-c[Asp-His-DPhe-Arg-Trp-Lys]-NH$_2$, which is a non-selective MC-1R, -3R, -4R, and -5R agonist (Dorr et al., *Life Sciences*, Vol. 58, 1777-1784, 1996). Drugs to treat erectile dysfunction act either peripherally or centrally and are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.*, 9: 115-121 (1997)]. MT-II is considered to be an "initiator" of the sexual response. The time to onset of erection with this drug is relatively short (10-20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route.

MT-II's erectogenic properties apparently are not limited to cases of psychogenic erectile dysfunction in that men with a variety of organic risk factors developed penile erections upon subcutaneous injection of the compound; moreover, the level of sexual desire was significantly higher after MT-II administration than after placebo [see H. Wessells, "Effect of an Alpha-Melanocyte Stimulating Hormone Analog on Penile Erection and Sexual Desire in Men with Organic Erectile Dysfunction," *Urology*, 56: 641-646 (2000)].

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine, piperidine and piperazine derivatives have been disclosed in U.S. Pat. Nos. 6,294,534, 6,350,760, 6,376,509, 6,410,548, 6,458,790, 6,472,398; in U.S. Patent Application Publication Nos. US2002/0004512, US2002/0019523, US2002/0137664, US 2003/0092732, US2003/0236262, US2003/0225060; and in International Patent Publications WO 99/64002, WO 00/74679, WO 01/058891, WO 01/70708, WO 01/70337, WO 01/91752, WO 02/015909, WO 02/067869, WO 02/068387, WO 02/068388, WO 02/079146, WO 03/007949, WO 03/009847, WO 03/057671, WO 03/066597, WO 03/068738, WO 03/092690, WO 04/024720, and WO 04/037797, as agonists of the melanocortin receptor(s) and particularly as selective agonists of the MC-4R receptor and thereby useful for the treatment of diseases and disorders, such as obesity, diabetes, and sexual dysfunction, including erectile dysfunction and female sexual dysfunction.

Other pharmacological approaches to the treatment of erectile dysfunction have been described [see, e.g., "Latest Findings on the Diagnosis and Treatment of Erectile Dysfunction," *Drug News & Perspectives*, 9: 572-575 (1996); "Oral Pharmacotherapy in Erectile Dysfunction," *Current Opinion in Urology*, 7: 349-353 (1997)].

Because of the unresolved deficiencies of the various pharmacological agents discussed above, there is a continuing need in the medical arts for improved methods and compositions to treat individuals suffering from psychogenic and/or organic sexual dysfunction. Such methods should have wider applicability, enhanced convenience and ease of compliance, short onset of action, reasonably long duration of action, and minimal side effects with few contraindications, as compared to agents now available. The instant invention addresses this problem by providing melanocortin receptor (MC-R) agonists, and in particular selective agonists of the melanocortin-4 receptor (MC-4R), useful in the treatment and prevention of sexual dysfunction, including male erectile dysfunction and female sexual dysfunction.

It is therefore an object of the present invention to provide acylated piperidine derivatives which are melanocortin receptor agonists and thereby useful to treat obesity, diabetes, male sexual dysfunction, and female sexual dysfunction.

It is another object of the present invention to provide acylated piperidine derivatives which are selective agonists of the melanocortin-4 (MC-4R) receptor.

It is another object of the present invention to provide pharmaceutical compositions comprising the melanocortin receptor agonists of the present invention with a pharmaceutically acceptable carrier.

It is another object of the present invention to provide methods for the treatment or prevention of disorders, diseases, or conditions responsive to the activation of the melanocortin-4 receptor in a mammal in need thereof by administering the compounds and pharmaceutical compositions of the present invention.

It is another object of the present invention to provide methods for the treatment or prevention of obesity, diabetes mellitus, male sexual dysfunction, and female sexual dysfunction by administering the compounds and pharmaceutical compositions of the present invention to a mammal in need thereof.

It is another object of the present invention to provide methods for the treatment of erectile dysfunction by administering the compounds and pharmaceutical compositions of the present invention to a mammal in need thereof.

These and other objects will become readily apparent from the detailed description that follows.

SUMMARY OF THE INVENTION

The present invention relates to novel 4-alkyl substituted piperidines of structural formula I:

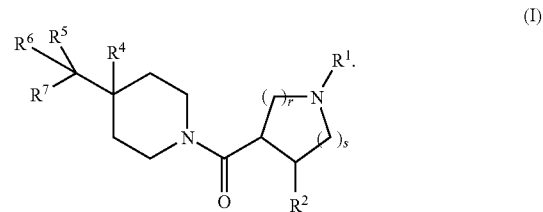

These piperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and female sexual dysfunction, in particular, male erectile dysfunction.

The present invention further relates to pharmaceutical compositions comprising the compounds of the present invention and a pharmaceutically acceptable carrier.

The present invention also relates to methods for the treatment or prevention of disorders, diseases, or conditions responsive to the activation of the melanocortin-4 receptor in a mammal in need thereof by administering the compounds and pharmaceutical compositions of the present invention.

The present invention also relates to methods for the treatment or prevention of obesity, diabetes mellitus, male sexual dysfunction, and female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat the condition.

The present invention also relates to methods for treating or preventing obesity by administering the compounds of the present invention in combination with a therapeutically effective amount of another agent known to be useful to prevent or treat the condition.

The present invention also relates to methods for treating or preventing diabetes by administering the compounds of the present invention in combination with a therapeutically effective amount of another agent known to be useful to prevent or treat the condition.

DETAILED DESCRIPTION OF THE INVENTION

The present invention relates to 4-substituted N-acylated piperidine derivatives useful as melanocortin receptor agonists, in particular, as selective MC-4R agonists. Compounds of the present invention are described by structural formula I:

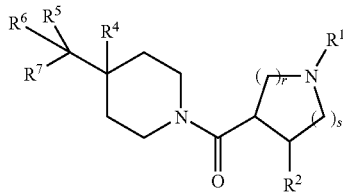

or a pharmaceutically acceptable salt thereof, wherein
$R^1$ is selected from the group consisting of:
   (1) hydrogen,
   (2) amidino,
   (3) —$C_{1-4}$ alkyliminoyl,
   (4) —$C_{1-8}$ alkyl,
   (5) —$(CH_2)_n$—$C_{3-7}$ cycloalkyl,
   (6) —$(CH_2)_n$heterocycloalkyl,
   (7) —$(CH_2)_n$-phenyl,
   (8) —$(CH_2)_n$-naphthyl, and
   (9) —$(CH_2)_n$-heteroaryl, wherein phenyl, naphthyl, and heteroaryl are unsubstituted or substituted with one to three substituents independently selected from $R^3$, and alkyl, cycloalkyl, and heterocycloalkyl are unsubstituted or substituted with one to three substituents independently selected from $R^3$ and oxo;
$R^2$ is selected from the group consisting of
   (1) phenyl,
   (2) naphthyl, and
   (3) heteroaryl, wherein phenyl, naphthyl, and heteroaryl are unsubstituted or substituted with one to three substituents independently selected from $R^9$;
each $R^3$ is independently selected from the group consisting of:
   (1) —$C_{1-8}$ alkyl,
   (2) —$(CH_2)_n$-phenyl,
   (3) —$(CH_2)_n$-heteroaryl,
   (4) —$(CH_2)_n$heterocycloalkyl,
   (5) —$(CH_2)_nC_{3-7}$ cycloalkyl,
   (6) halogen,
   (7) —$OR^8$,
   (8) —$(CH_2)_nC\equiv N$,
   (9) —$(CH_2)_nN(R^8)_2$,
   (10) —$(CH_2)_nC(O)N(R^8)_2$,
   (11) —$(CH_2)_nC(O)NR^8N(R^8)_2$,
   (12) —$(CH_2)_nC(O)NR^8NR^8C(O)R^8$, and
   (13) —$(CH_2)_nCF_3$, wherein phenyl and heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two substituents independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group;
$R^4$ is selected from the group consisting of:
   (1) hydrogen, and
   (2) —$C_{1-6}$ alkyl,
   (3) —$OC_{1-6}$ alkyl, and
   (4) —$(CH_2)_nN(R^8)C(O)R^8$;
$R^5$ is selected from the group consisting of:
   (1) —$CF_3$,
   (2) —$C_{1-6}$ alkyl,
   (3) —$C_{2-8}$ alkenyl,
   (4) —$C_{2-8}$ alkynyl,
   (5) —$OC_{1-8}$ alkyl,
   (6) —$(CH_2)_nC_{3-7}$ cycloalkyl,
   (7) —$(CH_2)_n$heterocycloalkyl,
   (8) —$(CH_2)_n$-phenyl,
   (9) —$(CH_2)_n$-naphthyl,
   (10) —$(CH_2)_n$-heteroaryl, and
   (11) —$(CH_2)_nC_{3-7}$ bicycloalkyl, wherein phenyl, naphthyl, and heteroaryl are unsubstituted or substituted with one to three substituents independently selected from $R^3$, and alkyl, alkenyl, alkynyl, cycloalkyl, heterocycloalkyl, and bicycloalkyl are unsubstituted or substituted with one to three substituents independently selected from $R^3$ and oxo, and wherein any methylene ($CH_2$) in $R^5$ is unsubstituted or substituted with one to two substituents independently selected from halogen, hydroxy, oxo, and $C_{1-4}$ alkyl;
$R^6$ is selected from the group consisting of:
   (1) hydrogen,
   (2) —$C_{1-6}$ alkyl, and
   (3) —$OC_{1-16}$ alkyl;
$R^7$ is selected from the group consisting of:
   (1) —$(CH_2)_nN(R^8)_2$,
   (2) —$(CH_2)_nNR^8C(O)R^8$,
   (3) —$(CH_2)_nOR^8$,
   (4) —$(CH_2)_nC\equiv N$,
   (5) —$(CH_2)_nC(O)OR^8$,
   (6) —$(CH_2)_nC(O)N(R^8)_2$,
   (7) —$(CH_2)_nNR^8C(O)N(R^8)_2$,
   (8) —$(CH_2)_nNR^8C(O)$heteroaryl,
   (9) —$(CH_2)_n$heteroaryl,
   (10) —$(CH_2)_nNR^8S(O)_pR^8$,
   (11) —$(CH_2)_nSR^8$, and
   (12) —$(CH_2)_nS(O)_pR^8$, wherein heteroaryl is unsubstituted or substituted with one to three substituents selected from $C_{1-4}$ alkyl; and any methylene ($CH_2$) in $R^7$ is unsubstituted or substituted with one to two substituents independently selected from halogen, hydroxy, oxo, and $C_{1-4}$ alkyl, or two $C_{1-4}$ alkyl substituents on any methylene ($CH_2$) in $R^7$ together with the atom to which they are attached form a 3, 4, 5, or 6-membered ring optionally containing an additional heteroatom selected from O, S, —NH, and —$NC_{1-4}$ alkyl;
each $R^8$ is independently selected from the group consisting of:
   (1) hydrogen,
   (2) —$C_{1-8}$ alkyl,
   (3) —$C_{2-8}$ alkenyl,
   (4) —$(CH_2)_nC_{3-7}$ cycloalkyl,
   (5) —$(CH_2)_n$heterocycloalkyl, (6) —(CH$_2$)$_n$-phenyl, and
(7) —(CH$_2$)$_n$-heteroaryl;
each R$^9$ is independently selected from the group consisting of:
(1) —C$_{1-8}$ alkyl,
(2) —C$_{2-8}$ alkenyl,
(3) —(CH$_2$)$_n$-phenyl,
(4) —(CH$_2$)$_n$-naphthyl,
(5) —(CH$_2$)$_n$-heteroaryl,
(6) —(CH$_2$)$_n$heterocycloalkyl,
(7) —(CH$_2$)$_n$C$_{3-7}$ cycloalkyl,
(8) halogen,
(9) —OR$^8$,
(10) —(CH$_2$)$_n$C(O)R$^8$,
(11) —(CH$_2$)$_n$OC(O)R$^8$,
(12) —(CH$_2$)$_n$C(O)OR$^8$,
(13) —(CH$_2$)$_n$C≡N,
(14) NO$_2$,
(15) —(CH$_2$)$_n$N(R$^8$)$_2$,
(16) —(CH$_2$)$_n$C(O)N(R$^8$)$_2$,
(17) —(CH$_2$)$_n$NR$^8$C(O)R$^8$,
(18) —(CH$_2$)$_n$NR$^8$C(O)OR$^8$,
(19) —(CH$_2$)$_n$NR$^8$C(O)-heteroaryl,
(20) —(CH$_2$)$_n$NR$^8$C(O)N(R$^8$)$_2$,
(21) —(CH$_2$)$_n$C(O)NR$^8$N(R$^8$)$_2$,
(22) —(CH$_2$)$_n$C(O)NR$^8$NR$^8$C(O)R$^8$,
(23) —(CH$_2$)$_n$NR$^8$S(O)$_p$R$^8$,
(24) —(CH$_2$)$_n$S(O)$_p$N(R$^8$)$_2$,
(25) —(CH$_2$)$_n$ S(O)$_p$R$^8$,
(26) —O(CH$_2$)$_n$C(O)N(R$^8$)$_2$,
(27) —(CH$_2$)$_n$CF$_3$, and
(28) —O(CH$_2$)$_n$CF$_3$, wherein alkenyl, phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and any methylene (CH$_2$) carbon atom in R$^9$ are unsubstituted or substituted with one to two substituents independently selected from halogen, hydroxy, oxo, C$_{1-4}$ alkyl, trifluoromethyl, and C$_{1-4}$ alkoxy, or two R$^9$ substituents on the same carbon atom are taken together with the carbon atom to form a cyclopropyl group;
r is 1 or 2;
s is 0, 1 or 2;
n is 0, 1, 2, 3, or 4; and
p is 0, 1, or 2.

In another embodiment of the compounds of the present invention, there are provided compounds of structural formula IIa or IIb of the indicated relative stereochemical configurations having the trans orientation of the phenyl and piperazinecarbonyl substituents:

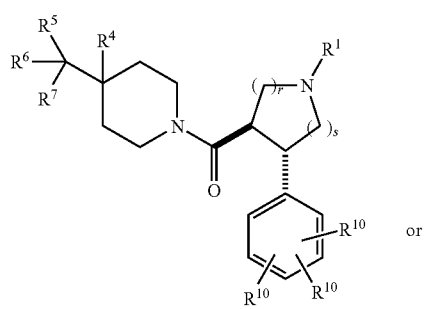

(IIa)

or

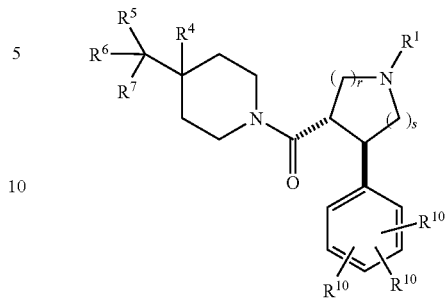

(IIb)

or a pharmaceutically acceptable salt thereof, wherein
R$^1$ is selected from the group consisting of: hydrogen, —C$_{1-4}$ alkyl, —(CH$_2$)$_{0-1}$ heterocycloalkyl, and —(CH$_2$)$_{0-1}$ phenyl;
R$^3$, R$^4$, R$^5$, R$^6$, R$^7$, R$^8$, r, s, n, and p are as defined in Claim 1;
each R$^{10}$ is independently selected from the group consisting of:
(1) hydrogen
(2) —C$_{1-8}$ alkyl,
(3) —C$_{2-8}$ alkenyl,
(4) —(CH$_2$)$_n$-phenyl,
(5) —(CH$_2$)$_n$-naphthyl,
(6) —(CH$_2$)$_n$-heteroaryl,
(7) —(CH$_2$)$_n$heterocycloalkyl,
(8) —(CH$_2$)$_n$C$_{3-7}$ cycloalkyl,
(9) halogen,
(10) —OR$^8$,
(11) —(CH$_2$)$_n$C(O)R$^8$,
(12) —(CH$_2$)$_n$OC(O)R$^8$,
(13) —(CH$_2$)$_n$C(O)OR$^8$,
(14) —(CH$_2$)$_n$C≡N,
(15) NO$_2$,
(16) —(CH$_2$)$_n$N(R$^8$)$_2$,
(17) —(CH$_2$)$_n$C(O)N(R$^8$)$_2$,
(18) —(CH$_2$)$_n$NR$^8$C(O)R$^8$,
(19) —(CH$_2$)$_n$NR$^8$C(O)OR$^8$,
(20) —(CH$_2$)$_n$NR$^8$C(O)-heteroaryl,
(21) —(CH$_2$)$_n$NR$^8$C(O)N(R$^8$)$_2$,
(22) —(CH$_2$)$_n$C(O)NR$^8$N(R$^8$)$_2$,
(23) —(CH$_2$)$_n$C(O)NR$^8$NR$^8$C(O)R$^8$,
(24) —(CH$_2$)$_n$NR$^8$S(O)$_p$R$^8$,
(25) —(CH$_2$)$_n$S(O)$_p$N(R$^8$)$_2$,
(26) —(CH$_2$)$_n$ S(O)$_p$R$^8$,
(27) —O(CH$_2$)$_n$C(O)N(R$^8$)$_2$,
(28) —(CH$_2$)$_n$CF$_3$, and
(29) —O(CH$_2$)$_n$CF$_3$, wherein alkenyl, phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and any methylene (CH$_2$) carbon atom in R$^{10}$ are unsubstituted or substituted with one to two substituents independently selected from halogen, hydroxy, oxo, C$_{1-4}$ alkyl, trifluoromethyl, and C$_{1-4}$ alkoxy, or two R$^{10}$ substituents on the same carbon atom are taken together with the carbon atom to form a cyclopropyl group.

In yet another embodiment of the compounds of the present invention, there are provided compounds of structural formula IIIa or IIIb of the indicated relative stereochemical configurations having the trains orientation of the phenyl and piperazinecarbonyl substituents:

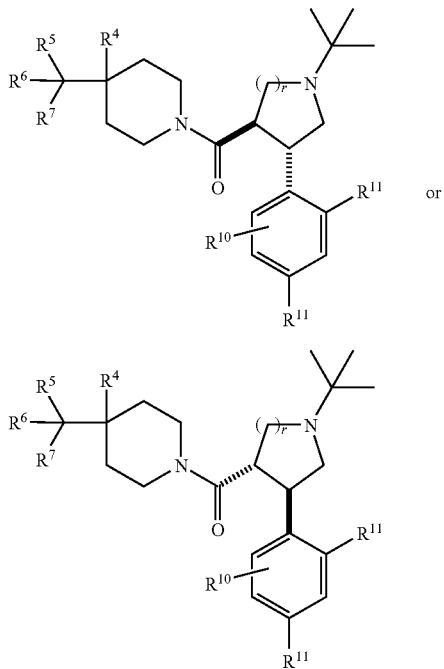

(IIIa)

(IIIb)

or a pharmaceutically acceptable salt thereof, wherein $R^3$, $R^4$, $R^5$, $R^6$, $R^7$, $R^8$, r, n, and p are as defined above; $R^{10}$ is selected from the group consisting of:
 (1) hydrogen,
 (2) —$C_{1-8}$ alkyl,
 (3) halogen,
 (4) —$OR^8$,
 (5) —$(CH_2)_nC\equiv N$,
 (6) —$(CH_2)_nS(O)R^8$,
 (7) —$(CH_2)_nCF_3$, wherein any alkyl and methylene ($CH_2$) carbon atom in $R^{10}$ is unsubstituted or substituted with one to two substituents independently selected from halogen, hydroxy, oxo, $C_{1-4}$ alkyl, trifluoromethyl, and $C_{1-4}$ alkoxy, or two $R^{10}$ substituents on the same carbon atom are taken together with the carbon atom to form a cyclopropyl group; and each $R^{11}$ is independently selected from the group consisting of:
 (1) —$C_{1-8}$ alkyl,
 (2) halogen,
 (3) —$OR^8$,
 (4) —$(CH_2)_nC\equiv N$,
 (5) —$S(O)R^8$,
 (6) —$(CH_2)_nCF_3$, wherein any alkyl and methylene ($CH_2$) carbon atom in $R^{11}$ is unsubstituted or substituted with one to two substituents independently selected from halogen, hydroxy, oxo, $C_{1-4}$ alkyl, trifluoromethyl, and $C_{1-4}$ alkoxy, or two $R^{11}$ substituents on the same carbon atom are taken together with the carbon atom to form a cyclopropyl group.

In a class of the embodiments of the present invention, $R^1$ is selected from the group consisting of: hydrogen, —$C_{1-4}$ alkyl, —$(CH_2)_{0-1}$ heterocycloalkyl, and —$(CH_2)_{0-1}$ phenyl.

In a subclass of this class, $R^1$ is selected from the group consisting of: —$C_{1-4}$ alkyl, and —$(CH_2)_{0-1}$ heterocycloalkyl. In another subclass of this class, $R^1$ is tert-butyl. In another subclass of this class, $R^1$ is —$(CH_2)_{0-1}$ heterocycloalkyl.

In another class of the embodiments of the present invention, $R^2$ is phenyl unsubstituted or substituted with one to three substituents independently selected from $R^9$. In another class of this embodiment, $R^2$ is phenyl substituted with one to three substituents independently selected from $R^9$. In another class of this embodiment, $R^2$ is phenyl substituted with two substituents independently selected from $R^9$. In another class of this embodiment, $R^2$ is 2,6-difluorophenyl. In yet another class of this embodiment, $R^2$ is 2-fluoro-6-chlorophenyl.

In another class of the embodiments of the present invention, each $R^3$ is independently selected from the group consisting of: —$C_{1-8}$ alkyl, —$(CH_2)_n$-phenyl, —$(CH_2)_n$-heteroaryl, —$(CH_2)_n$heterocycloalkyl, —$(CH_2)_nC_{3-7}$ cycloalkyl, fluoro, chloro, —$OR^8$, —$(CH_2)_nC\equiv N$, —$(CH_2)_nN(R^8)_2$, —$(CH_2)_nC(O)N(R^8)_2$, —$(CH_2)_nC(O)NR^8N(R^8)_2$, —$(CH_2)_nC(O)NR^8NR^8C(O)R^8$, and —$(CH_2)_nCF_3$, wherein phenyl and heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two substituents independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group.

In another class of the embodiments of the present invention, $R^4$ is hydrogen. In another class of this embodiment, $R^4$ is —$C_{1-4}$ alkyl.

In another class of the embodiments of the present invention, $R^5$ is selected from the group consisting of: —$CF_3$, —$C_{1-6}$alkyl, —$(CH_2)_nC_{3-7}$cycloalkyl, and —$(CH_2)_n$ phenyl, wherein phenyl is unsubstituted or substituted with one to three substituents independently selected from $R^3$, and alkyl and cycloalkyl are unsubstituted or substituted with one to three substituents independently selected from $R^3$ and oxo, and wherein any methylene ($CH_2$) in $R^5$ is unsubstituted or substituted with one to two substituents independently selected from halogen, hydroxy, oxo, and $C_{1-4}$ alkyl. In a subclass of this class, $R^5$ is selected from the group consisting of: —$CF_3$, —$(CH_2)_{0-1}C(CH_3)_3$; —$(CH_2)_{0-1}C(CH_3)_2$, —$(CH_2)_{0-1}CH(CH_2CH_3)_2$, —$(CH_2)_{0-1}$cyclobutyl, —$(CH_2)_{0-1}$cyclopentyl, —$(CH_2)_{0-1}$cyclohexyl, and —$(CH_2)_{0-1}$phenyl, wherein phenyl is unsubstituted or substituted with one to three substituents independently selected from $R^3$, wherein alkyl and cycloalkyl are unsubstituted or substituted with one to three substituents independently selected from $R^3$ and oxo, and wherein any methylene ($CH_2$) in $R^5$ is unsubstituted or substituted with one to two substituents independently selected from halogen, hydroxy, oxo, and $C_{1-4}$ alkyl. In another subclass of this class, $R^5$ is selected from the group consisting of: —$CF_3$, —$(CH_2)C(CH_3)_3$; —$(CH_2)_{0-1}CH(CH_3)_2$, —$CH(CH_2CH_3)_2$, -cyclobutyl, -cyclopentyl, -cyclohexyl, and -phenyl, wherein phenyl is unsubstituted or substituted with one to three substituents independently selected from $R^3$, wherein alkyl and cycloalkyl are unsubstituted or substituted with one to three substituents independently selected from $R^3$ and oxo, and wherein any methylene ($CH_2$) in $R^5$ is unsubstituted or substituted with one to two substituents independently selected from halogen, hydroxy, oxo, and $C_{1-4}$ alkyl. In yet another subclass of this class, $R^5$ is selected from the group consisting of: —$(CH_2)C(CH_3)_3$ and -cyclopentyl, wherein cyclopentyl is unsubstituted or substituted with one to three substituents independently selected from $R^3$ and oxo, and wherein any methylene ($CH_2$) in $R^5$ is unsubstituted or substituted with one to two substituents independently selected from halogen, hydroxy, oxo, and $C_{1-4}$ alkyl.

In another class of the embodiments of the present invention, $R^6$ is hydrogen. In yet another class of this embodiment, $R^6$ is —$C_{1-6}$ alkyl.

In another class of the embodiments of the present invention, $R^7$ is selected from the group consisting of —$(CH_2)_n$ $NR^8C(O)R^8$, —$(CH_2)_nOR^8$, —$(CH_2)_nC\equiv N$, —$(CH_2)_nC(O)$ $OR^8$, —$(CH_2)_nC(O)N(R^8)_2$, —$(CH_2)_nNR^8C(O)N(R^8)_2$, —$(CH_2)_nNR^8C(O)$heteroaryl, —$(CH_2)_n$heteroaryl, —$(CH_2)_n$ $NR^8S(O)_pR^8$, wherein heteroaryl is unsubstituted or substituted with one to three substituents selected from $C_{1-4}$ alkyl; and any methylene ($CH_2$) in $R^7$ is unsubstituted or substituted with one to two substituents independently selected from halogen, hydroxy, oxo, and $C_{1-4}$ alkyl, or two $C_{1-4}$ alkyl substituents on any methylene ($CH_2$) in $R^7$ together with the atom to which they are attached form a 3, 4, 5, or 6-membered ring optionally containing an additional heteroatom selected from O, S, —NH, and —$NC_{1-4}$ alkyl. In a subclass of this class, $R^7$ is selected from the group consisting of —$(CH_2)_{0-2}NR^8C(O)R^8$, —$(CH_2)_{0-32}R^8$, —$(CH_2)_{0-2}$ $C\equiv N$, —$(CH_2)_{0-2}C(O)OR^8$, —$(CH_2)_{0-2}C(O)N(R^8)_2$, —$(CH_2)_{0-2}NR^8C(O)N(R^8)_2$, —$(CH_2)_{0-2}NR^8C(O)$heteroaryl, —$(CH_2)_{0-2}$heteroaryl, —$(CH_2)_{0-2}NR^8S(O)_{0-2}R^8$, wherein heteroaryl is unsubstituted or substituted with one to three substituents selected from $C_{1-4}$ alkyl; and any methylene ($CH_2$) in $R^7$ is unsubstituted or substituted with one to two substituents independently selected from halogen, hydroxy, oxo, and $C_{1-4}$ alkyl, or two $C_{1-4}$ alkyl substituents on any methylene ($CH_2$) in $R^7$ together with the atom to which they are attached form a 3, 4, 5, or 6-membered ring optionally containing an additional heteroatom selected from O, S, —NH, and —$NC_{1-4}$ alkyl. In another subclass of this class, $R^7$ is —$(CH_2)_2NR^8C(O)R^8$, wherein any methylene ($CH_2$) in $R^7$ is unsubstituted or substituted with one to two substituents independently selected from halogen, hydroxy, oxo, and $C_{1-4}$ alkyl, or wherein two $C_{1-4}$ alkyl substituents on any methylene ($CH_2$) in $R^7$ together with the atom to which they are attached form a 3-membered ring.

In another class of the embodiments of the present invention, $R^9$ is selected from the group consisting of: hydrogen, —$C_{1-8}$ alkyl, halogen, —$OR^8$, —$(CH_2)_nC\equiv N$, —$(CH_2)_nS$ $(O)_pR^8$, —$CF_3$, wherein any alkyl and methylene ($CH_2$) carbon atom in $R^9$ is unsubstituted or substituted with one to two substituents independently selected from halogen, hydroxy, oxo, $C_{1-4}$ alkyl, trifluoromethyl, and $C_{1-4}$ alkoxy, or two $R^9$ substituents on the same carbon atom are taken together with the carbon atom to form a cyclopropyl group. In a subclass of this class, $R^9$ is selected from the group consisting of: hydrogen, —$C_{1-8}$ alkyl, fluoro, chloro, —$OCH_3$, —$C\equiv N$, —$S(O)$ $R^8$, —$CF_3$, wherein any alkyl is unsubstituted or substituted with one to two substituents independently selected from halogen, hydroxy, oxo, $C_{1-4}$ alkyl, trifluoromethyl, and $C_{1-4}$ alkoxy, or two $R^9$ substituents on the same carbon atom are taken together with the carbon atom to form a cyclopropyl group.

In another class of the embodiments of the present invention, $R^{10}$ is selected from the group consisting of: hydrogen, —$C_{1-8}$ alkyl, halogen, —$OR^8$, —$(CH_2)_nC\equiv N$, —$(CH_2)_n$ $S(O)_pR^8$, —$CF_3$, wherein any alkyl and methylene ($CH_2$) carbon atom in $R^{10}$ is unsubstituted or substituted with one to two substituents independently selected from halogen, hydroxy, oxo, $C_{1-4}$ alkyl, trifluoromethyl, and $C_{1-4}$ alkoxy, or two $R^{10}$ substituents on the same carbon atom are taken together with the carbon atom to form a cyclopropyl group. In a subclass of this class, $R^{10}$ is selected from the group consisting of: hydrogen, —$C_{1-8}$ alkyl, fluoro, chloro, —$OCH_3$, —$C\equiv N$, —$S(O)R^8$, —$CF_3$, wherein any alkyl is unsubstituted or substituted with one to two substituents independently selected from halogen, hydroxy, oxo, $C_{1-4}$ alkyl, trifluoromethyl, and $C_{1-4}$ alkoxy, or two $R^{10}$ substituents on the same carbon atom are taken together with the carbon atom to form a cyclopropyl group.

In another class of the embodiments of the present invention, $R^{11}$ is selected from the group consisting of: hydrogen, —$C_{1-8}$ alkyl, fluoro, chloro, —$OCH_3$, —$C\equiv N$, —$S(O)R^8$, —$CF_3$, wherein any alkyl is unsubstituted or substituted with one to two substituents independently selected from halogen, hydroxy, oxo, $C_{1-4}$ alkyl, trifluoromethyl, and $C_{1-4}$ alkoxy, or two $R^{11}$ substituents on the same carbon atom are taken together with the carbon atom to form a cyclopropyl group. In a subclass of this class, both $R^{11}$ substituents are fluorine In another class of the embodiments of the present invention, r is 1 and s is 1. In another class of this embodiment of the compounds of structural formula I, r is 2 and s is 1.

In another class of the embodiments of the present invention, n is 0, 1, and 2. In another class of this embodiment of the compounds of structural formula I, p is 0.

Illustrative, but nonlimiting, examples of compounds of the present invention that are useful as melanocortin-4 receptor agonists are the following:

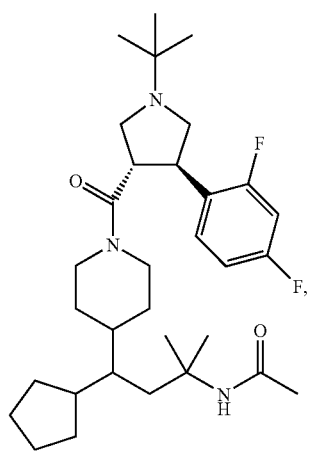

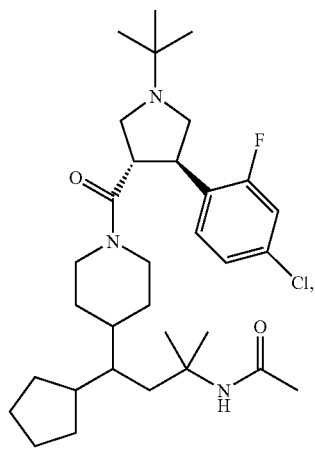

-continued
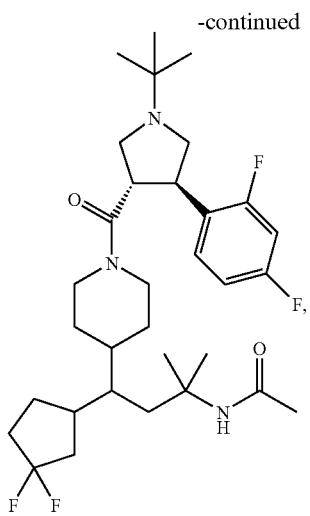
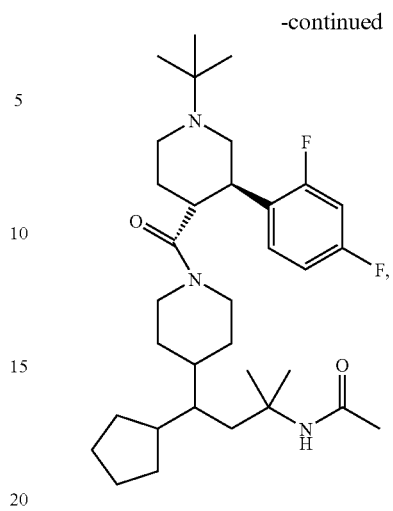
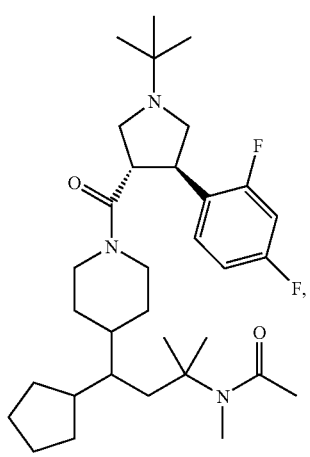
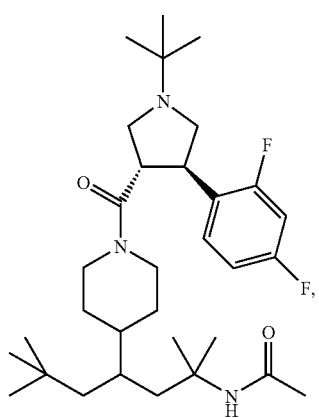
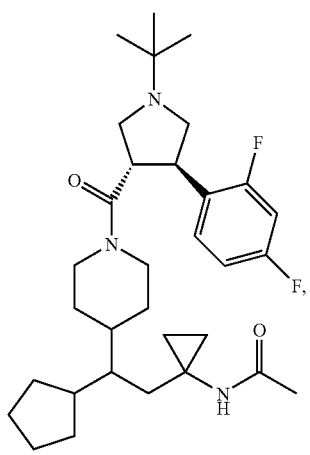
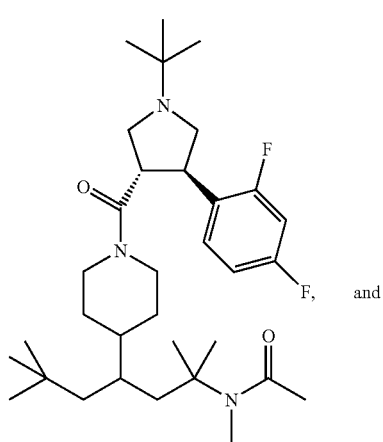 and

-continued

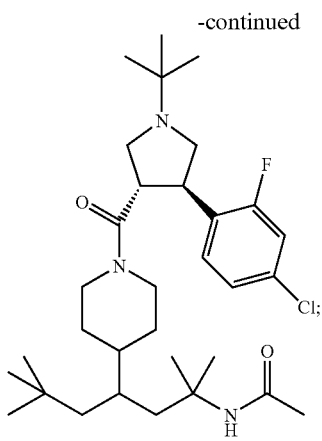

and pharmaceutically acceptable salts thereof.

The compounds of structural formula I are effective as melanocortin receptor ligands and are particularly effective as selective agonists of MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

One aspect of the present invention provides a method for the treatment or prevention of disorders, diseases or conditions responsive to the activation of the melanocortin-4 receptor in a mammal in need thereof which comprises administering to the mammal a therapeutically or prophylactically effective amount of a compound of structural formula I.

Another aspect of the present invention provides a method for the treatment or prevention of obesity in a mammal in need thereof which comprises administering to said mammal a therapeutically or prophylactically effective amount of a compound of structural formula I. Another aspect of the present invention provides a method for the treatment or prevention of diabetes in a mammal in need thereof which comprises administering to said mammal a therapeutically or prophylactically effective amount of a compound of structural formula I.

Yet another aspect of the present invention provides a method for the treatment or prevention of obesity which comprises administering to a mammal in need of such treatment or prevention a therapeutically or prophylactically effective amount of a compound of structural formula I in combination with a therapeutically effective amount of another agent known to be useful for the treatment of this condition. Another aspect of the present invention provides a method of treating or preventing diabetes or obesity in a mammal in need thereof comprising administering to the mammal a therapeutically effective amount of a compound of structural formula I in combination with an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, a ghrelin receptor antagonist, or a dipeptidyl peptidase IV inhibitor. Another aspect of the present invention provides a method of treating or preventing an obesity-related disorder selected from the group consisting of overeating, binge eating, and bulimia, hypertension, diabetes, elevated plasma insulin concentrations, insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, metabolic syndrome, insulin resistance syndrome, sexual and reproductive dysfunction, infertility, hypogonadism, hirsutism, obesity-related gastro-esophageal reflux, Pickwickian syndrome, cardiovascular disorders, inflammation, systemic inflammation of the vasculature, arteriosclerosis, hypercholesterolemia, hyperuricaemia, lower back pain, gallbladder disease, gout, and kidney cancer, cardiac hypertrophy and left ventricular hypertrophy, in a mammal in need thereof which comprises administering to the mammal a therapeutically or prophylactically effective amount of a compound of structural formula I.

Yet another aspect of the present invention provides a pharmaceutical composition of a compound of structural formula I further comprising a second active ingredient selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, a ghrelin receptor antagonist, and a dipeptidyl peptidase IV inhibitor.

Another aspect of the present invention provides a method for the treatment or prevention of male or female sexual dysfunction in a mammal in need thereof comprising administering to the mammal a therapeutically or prophylactically effective amount of a compound of structural formula I. Another aspect of the present invention provides a method for the treatment or prevention of erectile dysfunction in a mammal in need thereof comprising administering to the mammal a therapeutically or prophylactically effective amount of a compound of structural formula I.

Another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I in combination with a therapeutically effective amount of another agent known to be useful for the treatment of these conditions. Another aspect of the present invention provides a method of treating erectile dysfunction in a mammal in need thereof comprising administering to the mammal a therapeutically effective amount of a compound structural formula I in combination with a type V cyclic-GMP-selective phosphodiesterase inhibitor, an $α_2$-adrenergic receptor antagonist, or a dopaminergic agent. Yet another aspect of the present invention provides a pharmaceutical composition of a compound structural formula I further comprising a second active ingredient selected from the group consisting of a type V cyclic-GMP-selective phosphodiesterase inhibitor, an $α_2$-adrenergic receptor antagonist, and a dopaminergic agent.

Yet another aspect of the present invention provides a pharmaceutical composition comprising a compound of structural formula I and a pharmaceutically acceptable carrier.

Yet another aspect of the present invention relates to the use of a compound of formula I for the manufacture of a medicament useful for the treatment or prevention, or suppression of a disease mediated by the melanocortin-4 receptor in a mammal in need thereof. Yet another aspect of the present invention relates to the use of a compound of formula I for the manufacture of a medicament useful for the treatment or prevention, or suppression of obesity in a mammal in need thereof. Another aspect of the invention relates to the use of a compound of formula I for the manufacture of a medicament useful for the treatment or prevention of an obesity-related disorder selected from the group consisting of overeating, binge eating, and bulimia, hypertension, diabetes, elevated plasma insulin concentrations, insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, metabolic syndrome, insulin resistance syndrome, sexual and reproductive dysfunction, infertility, hypogonadism, hirsutism, obesity-related gastro-esophageal reflux, Pickwickian syndrome, cardiovascular disorders, inflammation, systemic inflammation of the vasculature, arteriosclerosis, hypercholesterolemia, hyperuricaemia, lower back pain, gallbladder disease, gout, and kidney cancer, cardiac hypertrophy and left ventricular hypertrophy. Yet another aspect of the present invention relates to the use of a compound of formula I for the manufacture of a medicament useful for the treatment or prevention, or suppression of diabetes in a mammal in need thereof. Yet another aspect of the present invention relates to the use of a compound of formula I for the manufacture of a medicament useful for the treatment or prevention, or suppression of male sexual dysfunction and female sexual dysfunction in a mammal in need thereof. Yet another aspect of the present invention relates to the use of a compound of formula I for the manufacture of a medicament useful for the treatment or prevention, or suppression of male erectile dysfunction in a mammal in need thereof.

Melanocortin receptor agonist compounds can be provided in kit. Such a kit typically contains an active compound in dosage forms for administration. A dosage form contains a sufficient amount of active compound such that a beneficial effect can be obtained when administered to a subject during regular intervals, such as 1 to 6 times a day, during the course of 1 or more days. Preferably, a kit contains instructions indicating the use of the dosage form for weight reduction (e.g., to treat obesity or overweight) or sexual dysfunction, and the amount of dosage form to be taken over a specified time period.

Throughout the instant application, the following terms have the indicated meanings:

The term "alkyl", as well as other groups having the prefix "alk", such as alkoxy, alkanoyl, means carbon chains of the designated length which may be in a straight or branched configuration, or combinations thereof. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

The term "alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

The term "halogen" includes fluorine, chlorine, bromine and iodine.

The term "$C_{1-4}$ alkyliminoyl" means $C_{1-3}C(=NH)-$.

The term "aryl" includes mono- or bicyclic aromatic rings containing only carbon atoms. Examples of aryl include phenyl and naphthyl.

The term "heteroaryl" includes mono- and bicyclic aromatic rings containing from 1 to 4 heteroatoms selected from nitrogen, oxygen and sulfur. Examples thereof include, but are not limited to, pyridinyl, furyl, furanyl, thienyl, pyrrolyl, oxazolyl, thiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like. In one embodiment of the present invention, heteroaryl is selected from the group consisting of pyridinyl, furyl, furanyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl. Bicyclic heteroaromatic rings include, but are not limited to, benzothiadiazole, indole, benzothiophene, benzofuran, benzimidazole, benzisoxazole, benzothiazole, quinoline, quinazoline, benzotriazole, benzoxazole, isoquinoline, isoindoline, purine, furopyridine, thienopyridine, benzisodiazole, triazolopyrimidine, and 5,6,7,8-tetrahydroquinoline.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, and cycloheptyl.

The term "heterocycloalkyl" is intended to include 3 to 10 membered mono- and bicyclic non-aromatic heterocycles containing one to four heteroatoms selected from nitrogen, oxygen and sulfur. Examples of heterocycloalkyls include, but are not limited to, azetidine, piperidine, morpholine, thiamorpholine, pyrrolidine, imidazolidine, tetrahydrofuran, piperazine, 1-thia-4-aza-cyclohexane, 1-aza-4-thia-cyclohexane, and 1,3 oxazolidine.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

The term "subject" means a mammal. One embodiment of the term "mammal" is a "human," said human being either male or female. As such, the term "mammal" includes, but is not limited to, companion animals such as cats and dogs, as well as horses.

The terms "subject in need thereof" or "mammal in need thereof" refer to a mammal who is in need of treatment or prophylaxis as determined by a researcher, veterinarian, medical doctor or other clinician.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity with which agonists vary, in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers—Diastereomers—Geometric Isomers—Tautomers

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I. Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or diastereomer of a compound of the general formulae I, IIa, IIb, IIIa, and IIIb may be obtained by stereospecific synthesis using optically pure starting materials or reagents of known absolute configuration.

Some of the compounds described herein may exist as tautomers such as keto-enol tautomers. The individual tautomers as well as mixtures thereof are encompassed within the compounds of structural formula I. Some of the compounds described herein contain olefinic double bonds, and unless specified otherwise, are meant to include both E and Z geometric isomers.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts, such as the hydrochloride salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity, diabetes mellitus, hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction, fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor (MC-4R) relative to MC-1R, MC-2R, MC-3R, and MC-5R, which makes them especially useful in the prevention and treatment of obesity, as well as male and/or female sexual dysfunction, including erectile dysfunction.

The compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, and increased anesthetic risk. The compositions of the present invention are also useful for reducing the risk of secondary outcomes of obesity, such as reducing the risk of left ventricular hypertrophy. The compositions of the present invention are also useful to treat Alzheimer's disease.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-II.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese.

The compositions of the present invention are useful for treating both Type I and Type II diabetes. The compositions are especially effective for treating Type II diabetes. The compounds or combinations of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of treatment may be decreasing plasma triglycerides in a subject with elevated plasma triglycerides. Another outcome of treatment may be lowering LDL cholesterol in a subject with high LDL cholesterol levels. Another outcome of treatment may be increasing HDL cholesterol in a subject with low HDL cholesterol levels. Another outcome may be decreasing the LDL/HDL ratio in a subject in need thereof. Another outcome of treatment may be increasing insulin sensitivity. Another outcome of treatment may be enhancing glucose tolerance in a subject with glucose intolerance. Another outcome of treatment may be decreasing insulin resistance in a subject with increased insulin resistance or elevated levels of insulin. Another outcome may be decreasing triglycerides in a subject with elevated triglycerides. Yet another outcome may be improving LDL cholesterol, non-HDL cholesterol, triglyceride, HDL cholesterol or other lipid analyte profiles.

Prevention of diabetes mellitus refers to the administration of a compound or combination of the present invention to prevent the onset of diabetes in a mammal at risk thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, dermatological disorders, hypertension, insulin resistance, hypercholesterolemia, hypertriglyceridemia, and cholelithiasis.

"Male sexual dysfunction" includes impotence, loss of libido, and erectile dysfunction.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

Treatment of male sexual dysfunction refers to the administration of a compound or combination of the present invention to treat impotence and/or loss of libido, and/or erectile dysfunction in a male mammal in need thereof. One outcome of treatment may be a decrease in impotence. Another outcome of treatment may be an increase in libido. Yet another outcome of treatment may be a decrease in the magnitude or frequency of erectile dysfunction.

Treatment of male sexual dysfunction refers to the administration of a compound or combination of the present invention to treat one or more of the symptoms of male sexual dysfunction in a male mammal in need thereof. One outcome of treatment may be increasing the ability to achieve an erection. Another outcome of treatment may be increasing the ability to maintain an erection. Another outcome of treatment may be reducing ejaculatory failure. Another outcome of treatment may be decreasing premature ejaculation. Yet another outcome of treatment may be increasing the ability to achieve an orgasm.

Prevention of male sexual dysfunction and male erectile dysfunction refers to the administration of the compounds or combinations of the present invention to prevent the symptoms of sexual dysfunction and erectile dysfunction in a male mammal at risk thereof.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

The terms "administration of" and or "administering" a compound should be understood to mean providing a compound of the invention or a prodrug of a compound of the invention to a subject in need of treatment.

The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art.

The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder.

The therapeutically or prophylactically effective amount, or dosage, of an individual compound is determined, in the final analysis, by the physician in charge of the case, but depends on factors such as the exact disease to be treated, the severity of the disease and other diseases or conditions from which the subject suffers, the chosen route of administration, other drugs and treatments which the subject may concomitantly require, and other factors in the physician's judgment.

Administration and Dose Ranges

Any suitable route of administration may be employed for providing a mammal, especially a human with an effective amount, or dosage, of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response. It may be necessary to use dosages outside these limits in some cases.

When treating diabetes mellitus and/or hyperglycemia, as well as other diseases or disorders, including obesity-related disorders, for which compounds of formula I are useful, generally satisfactory results are obtained when the compounds of the present invention are administered at a daily dosage of from about 0.001 milligram to about 100 milligram per kilogram of body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response. It may be necessary to use dosages outside these limits in some cases.

For the treatment of sexual dysfunction compounds of the present invention are given in a dose range of 0.001 milligram to about 100 milligram per kilogram of body weight, preferably as a single dose orally or as a nasal spray.

In the case where an oral composition is employed, a suitable dosage range is, e.g. from about 0.01 mg to about 1500 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750, 1000, 1250 or 1500 milligrams of the active ingredient for the symptomatic adjustment of the dosage to the subject to be treated.

For use where a composition for intravenous administration is employed, a suitable dosage range is from about 0.001 mg to about 100 mg (preferably from 0.01 mg to about 50 mg, more preferably 0.1 mg to 10 mg) of a compound of Formula I per kg of body weight per day. This dosage regimen may be adjusted to provide the optimal therapeutic response. It may be necessary to use dosages outside these limits in some cases.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual subject. Such dosage may be ascertained readily by a person skilled in the art.

Combination Therapy

Compounds of structural formula I may be used in combination with other drugs that are used in the treatment/prevention/suppression or amelioration of the diseases or conditions for which compounds of structural formula I are useful. Such other drugs may be administered, by a route and in an amount commonly used therefor, contemporaneously or sequentially with a compound of structural formula I. When a compound of structural formula I is used contemporaneously with one or more other drugs, a pharmaceutical composition containing such other drugs in addition to the compound of structural formula I is preferred. When a composition of the present invention is used contemporaneously with one or more other drugs, a pharmaceutical composition in unit dosage form containing such other drugs and the composition of the present invention is preferred. However, the combination therapy also includes therapies in which the composition of the present invention and one or more other drugs are administered on different overlapping schedules. It is also contemplated that when used in combination with one or more other active ingredients, the composition of the present invention and the other active ingredients may be used in lower doses than when each is used singly. Accordingly, the pharmaceutical compositions of the present invention include those that also contain one or more other active ingredients, in addition to a compound of structural formula I.

Examples of other active ingredients that may be combined with a compound of structural formula I for the treatment or prevention of obesity and/or diabetes, either administered separately or in the same pharmaceutical compositions, include, but are not limited to:

(a) insulin sensitizers including (i) PPARγ agonists such as the glitazones (e.g. ciglitazone; darglitazone; troglitazone, pioglitazone, englitazone, isaglitazone (MCC-555), BRL49653, rosiglitazone; CLX-0921; 5-BTZD), GW-0207, LG-100641, and LY-300512, and the like), and compounds disclosed in WO97/10813, WO97/27857, 97/28115, 97/28137 and 97/27847;

ii) biguanides such as metformin (Glucophage®), buformin, and phenformin;

(b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)—$NH_2$);

(c) sulfonylureas, such as tolbutamide and glipizide, acetohexamide; chlorpropamide; diabinese; glibenclamide; glyburide; glimepiride; gliclazide; glipentide; gliquidone; glisolamide; and tolazamide;

(d) α-glucosidase inhibitors (such as acarbose, adiposine; camiglibose; emiglitate; miglitol; voglibose; pradimicin-Q; salbostatin; CKD-711; MDL-25,637; MDL-73,945; and MOR 14, and the like);

(e) cholesterol lowering agents such as (i) HMG-CoA reductase inhibitors (lovastatin, simvastatin, pravastatin, fluvastatin, atorvastatin, itavastatin, rivastatin, rosuvastatin, ZD-4522, and other statins), (ii) sequestrants (cholestyramine, colestipol and a dialkylaminoalkyl derivatives of a cross-linked dextran, colesevelum, Colestid®; LoCholest®, and the like, (ii) nicotinyl alcohol nicotinic acid or a salt thereof, (iii) proliferator-activator receptor α agonists such as fenofibric acid derivatives (gemfibrozil, clofibrate, fenofibrate and benzafibrate), (iv) inhibitors of cholesterol absorption for example beta-sitosterol, stanol esters, sterol glycosides such as tiqueside; and azetidinones such as ezetimibe, efucimibe, KY 505, SMP797, and the like, and (acyl CoA:cholesterol acyltransferase) inhibitors for example melinamide, and avasimibe, (v) anti-oxidants such as probucol, (vi) vitamin E, (vii) thyromimetics; (viii) Zetia; and (ix) Vytorin;

(f) PPARδ agonists, such as those disclosed in WO97/28149, and such as GW 501516, and GW 590735, and the like;

(g) anti-obesity serotonergic agents, such as fenfluramine, dexfenfluramine, phentermine, and sibutramine;

(h) β3-adrenoreceptor agonists, such as AD9677/TAK677 (Dainippon/Takeda), CL-316,243, SB 418790, BRL-37344, L-796568, BMS-196085, BRL-35135A, CGP12177A, GW 427353, BTA-243, Trecadrine, Zeneca D7114, SR 59119A, and such as those disclosed in U.S. Pat. Nos. 5,705,515, and 5,451,677 and PCT Patent Publications WO94/18161, WO95/29159, WO97/46556, WO98/04526 and WO98/32753, WO 01/74782, and WO 02/32897;

(i) pancreatic lipase inhibitors, such as orlistat (Xenical®), Triton WR1339, RHC80267, lipstatin, tetrahydrolipstatin, teasaponin, diethyl-umbelliferyl phosphate, FL-386, WAY-121898, Bay-N-3176, valilactone, esteracin, ebelactone A, ebelactone B, and RHC 80267, and those disclosed in PCT Application No. WO 01/77094, and U.S. Pat. Nos. 4,598,089, 4,452,813, 5,512,565, 5,391,571, 5,602,151, 4,405,644, 4,189,438, and 4,242,453;

(j) feeding behavior modifying agents, such as neuropeptide Y Y1 and Y5 antagonists, such as those disclosed in WO 97/19682, WO 97/20820, WO 97/20821, WO 97/20822, WO 97/20823, WO 01/14376, and U.S. Pat. No. 6,191,160; neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528;

and neuropeptide Y5 antagonists, such as 152,804, GW-569180A, GW-594884A, GW-587081X, GW-548118x, FR235,208, FR226928, FR 240662, FR252384, 1229 U91, GI-264879A, CGP71683A, LY-377897, LY-366377, PD-160170, SR-120562A, SR-120819A, JCF-104, and H409/22; and those disclosed in U.S. Pat. Nos. 6,140,354, 6,191,160, 6,258,837, 6,313,298, 6,337,332, 6,329,395, 6,326,375, 6,335,345, and 6,340,683, European Patent Nos. EP-01010691, and EP-01044970, and PCT Patent Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648 and WO 02/094789; and Norman et al., J. Med. Chem. 43:4288-4312 (2000);

(k) orexin-1 receptor antagonists, such as SB-334867-A, and those disclosed in PCT Patent Application Nos. WO 01/96302, WO 01/68609, WO 02/51232, WO 02/51838, and WO 03/023561;

(l) PPARα agonists such as described in WO 97/36579 by Glaxo, and PPARα agonists such as beclofibrate, benzafibrate, ciprofibrate, clofibrate, etofibrate, fenofibrate, gemcabene, gemfibrozil, GW 7647, BM 170744, and LY518674; and other fibric acid derivatives, such as Atrornid®, Lopid® and Tricor®, and the like;

(m) PPARγ antagonists as described in WO97/10813;

(n) serotonin reuptake inhibitors such as fluoxetine, paroxetine, and sertraline;

(O) growth hormone secretagogues, such as MK-0677, and growth hormone secretagogue receptor agonists/antagonists, such as NN703, hexarelin, SM-130686, CP-424,391, L-692,429 and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888;

(p) cannabinoid receptor ligands, such as cannabinoid $CB_1$ receptor antagonists or inverse agonists, such as rimonabant (Sanofi Synthelabo), and SR-147778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/0060007, and WO 03/007887; and EPO Application No. EP-658546, EP-656354, EP-576357;

(q) protein tyrosine phosphatase-1B (PTP-1B) inhibitors; and (r) anti-obesity agents, such as (1) melanin-concentrating hormone (MCH) receptor antagonists, such as those disclosed in WO 01/21577 and WO 01/21169; (2) melanin-concentrating hormone 1 receptor (MCH1R) antagonists, such as T-226296 (Takeda), SNP-7941, and those disclosed in PCT Patent Application Nos. WO 01/82925, WO 01/87834, WO 02/051809, WO 02/06245, WO 02/04433, WO 02/076929, WO 02/076947, WO 02/51809, WO 02/083134, WO 02/094799, and WO 03/004027, and Japanese Patent Application No. JP 13226269; (3) melanin-concentrating hormone 2 receptor (MCH2R) agonist/antagonists; (4) serotonin reuptake inhibitors such as fluoxetine, paroxetine, and sertraline, and those disclosed in U.S. Patent Application No. 6,365,633, and PCT Patent Application Nos. WO 01/27060 and WO 01/162341; (5) melanocortin agonists, such as Melanotan II or those described in WO 99/64002 and WO 00/74679; (6) other Mc4r (melanocortin 4 receptor) agonists, such as CHIR86036 (Chiron), ME-10142, and ME-10145 (Melacure), and those disclosed in PCT Application Nos. WO 01/991752, WO 01/74844, WO 02/12166, WO 02/11715, and WO 02/12178; (7) 5HT-2 agonists; (8) 5HT2C (serotonin receptor 2C) agonists, such as BVT933, DPCA37215, WAY161503, R-1065, IK264, and PNU 22394, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (9) galanin antagonists; (10) CCK agonists; (11) CCK-A (cholecystokinin -A) agonists, such as AR-R 15849, GI 181771, JMV-180, A-71378, A-71623 and SR146131, and those described in U.S. Pat. No. 5,739,106; (12) GLP-1 (glucagon like peptide 1 agonists; (13) corticotropin-releasing hormone agonists; (14) histamine receptor-3 (H3) modulators; (15) histamine receptor-3 (H3) antagonists/inverse agonists, such as hioperamide, 3-(1H-imidazol-4-yl) propyl N-(4-pentenyl)carbamate, clobenpropit, iodophenpropit, imoproxifan, GT2394 (Gliatech), A 331440, and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (16) 11β-hydroxy steroid dehydrogenase-1 inhibitors (11β-HSD-1), such as BVT 3498, BVT 2733, and those compounds disclosed in WO 01/90091, WO 01/90090, WO 01/90092; (17) PDE (phosphodiesterase) inhibitors, such as theophylline, pentoxifylline, zaprinast, sildenafil, amrinone, milrinone, cilostamide, rolipram, and cilomilast; (18) phosphodiesterase-3B (PDE3B) inhibitors; (19) NE (norepinephrine) transport inhibitors, such as GW 320659, despiramine, talsupram, and nomifensine; (20) ghrelin receptor antagonists, such as those disclosed in PCT Application Nos. WO 01/87335, and WO 02/08250; (21) leptin, including recombinant human leptin (PEG-OB, Hoffman La Roche) and recombinant methionyl human leptin (Amgen); (22) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (23) BRS3 (bombesin receptor subtype 3) agonists; (24) CNTF (Ciliary neurotrophic factors), such as GI-181771 (Glaxo-SmithKline), SR146131 (Sanofi Synthelabo), butabindide, PD170,292, and PD 149164 (Pfizer); (25) CNTF derivatives, such as axokine (Regeneron), and those disclosed in PCT Application Nos. WO 94/09134, WO 98/22128, and WO 99/43813; (26) monoamine reuptake inhibitors, such as sibutramine (Meridia®/Reductil®), and those disclosed in U.S. Pat. Nos. 4,746,680, 4,806,570, and 5,436,272, and U.S. Patent Publication No. 2002/0006964, WO 01/27068, and WO 01/62341; (27) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (28) thyroid hormone β agonists, such as KB-2611 (KaroBioBMS), and those disclosed in PCT Application No. WO 02/15845, and Japanese Patent Application No. JP 2000256190; (29) FAS (fatty acid synthase) inhibitors, such as Cerulenin and C75; (30) DGAT1 (diacylglycerol acyltransferase 1) inhibitors; (31) DGAT2 (diacylglycerol acyltransferase 2) inhibitors; (32) ACC2 (acetyl-CoA carboxylase-2) inhibitors; (33) glucocorticoid antagonists; (34) acyl-estrogens, such as oleoyl-estrone, disclosed in del Mar-Grasa, M. et al., Obesity Research, 9:202-9 (2001); (35) dipeptidyl peptidase IV (DP-IV) inhibitors, such as isoleucine thiazolidide, valine pyrrolidide, NVP-DPP728, LAF237, P32/98P93/01, TSL 225, TMC-2A/2B/2C, FE 999011, P9310/K364, VIP 0177, SDZ 274-444; and the compounds disclosed in WO 03/004498, WO 03/004496, EP 1 258 476, WO 02/083128, WO 02/062764, WO 03/000250, WO 03/002530, WO 03/002531, WO 03/002553, WO 03/002593, WO 03/000180, and WO 03/000181; NVP-DPP728; P32/98; LAF 237, TSL 225, valine pyrrolidide, TMC-2A/2B/2C, CD-26 inhibitors, FE 999011, P9310/K364, VIP 0177, DPP4, SDZ 274-444; and the compounds disclosed in WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (36) fatty acid transporter inhibitors; (37) dicarboxylate transporter inhibitors; (38) glucose transporter inhibitors; (39) phosphate transporter inhibitors; (40) Topiramate (Topimax®); (41) 5HT (serotonin) transporter inhibitors, such as paroxetine, fluoxetine, fluvoxamine, sertraline, and imipramine; (42) opioid antagonists, such as nalmefene (Revex®), 3-methoxynaltrexone, naloxone, and naltrexone; and those disclosed in WO 00/21509; (43) Mc3r (melanocortin 3 receptor) agonists; (44) phytophann compound 57 (CP 644,673); (45) FAS (fatty acid synthase) inhibitors, such as Cerulenin and C75; (46) SCD-1 (stearoyl-CoA desaturase-1) inhibitors; and the like; (47) a minorex; (48) amphechloral; (49) amphetamine; (50) benzphetamine; (51) chlorphentermine; (52) clobenzorex; (53) cloforex; (54) clominorex; (55) clortermine; (56) cyclexedrine; (57) dextroamphetamine; (58) diethylpropion; (59) diphemethoxidine, (60) N-ethylamphetamine; (61) fenbutrazate; (62) fenisorex; (63) fenproporex; (64) fludorex; (65) fluminorex; (66) furfurylmethylamphetamine; (67) levamfetamine; (68) levophacetoperane; (69) mazindol; (70) mefenorex; (71) metamfepramone; (72) methamphetamine; (norpseudoephedrine; (73) pentorex; (74) phendimetrazine; (75) phenmetrazine; (76) phenylpropanolamine; (77) picilorex; and (78) zonisamide; (79) PYY, PYY3-36, and PYY agonists such as those disclosed in WO 03/026591; and the like;

(s) lipid lowering agents such as (1) CETP inhibitors such as JTT 705, torcetrapib, CP 532,632 BAY63-2149, SC 591, SC 795, and the like; (2) squalene synthetase inhibitors; (3) FXR receptor modulators such as GW 4064, SR 103912, and the like; (4) LXR receptor such as GW 3965, T9013137, and XTCO179628, and the like; (5) lipoprotein synthesis inhibitors such as niacin; (6) renin angiotensin system inhibitors; (7) PPAR δ partial agonists; (8) bile acid reabsorption inhibitors, such as BARI 1453, SC435, PHA384640, S8921, AZD7706, and the like; (9) triglyceride synthesis inhibitors; (10) microsomal triglyceride transport (MTTP) inhibitors, such as inplitapide, LAB687, and CP346086, and the like; (11) transcription modulators; (12) squalene epoxidase inhibitors; (13) low density lipoprotein (LDL) receptor inducers; (14) platelet aggregation inhibitors; (15) 5-LO or FLAP inhibitors; and (16) niacin receptor agonists;

(t) anti-diabetic agents such as (1) meglitinides such as repaglinide, and nateglinide, and the like; (2) alpha-amylase inhibitors such as tendamistat, trestatin, and Al-3688, and the like; (3) insulin secreatagogues such as linogliride; and A-4166, and the like; (4) fatty acid oxidation inhibitors, such as clomoxir, and etomoxir, and the like; (5) A2 antagonists, such as midaglizole; isaglidole; deriglidole; idazoxan; earoxan; and fluparoxan, and the like; (6) non-thiazolidinediones such as JT-501, and farglitazar (GW-2570/GI-262579), and the like; (7) PPARα/γ dual agonists such as CLX-0940, GW-1536, GW1929, GW-2433, KRP-297, L-796449, LR-90, SB 219994, MK-767, and muraglitazar, and the like; (8) other insulin sensitizing drugs; and (9) VPAC2 receptor agonists; and (u) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like;

(4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as candesartan, eprosartan, irbesartan, losartan (Hyzaar, Cozaar), pratosartan, tasosartan, telmisartan, valsartan, and EXP-3137, F16828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; and (12) aldosterone inhibitors, and the like.

Examples of other anti-obesity agents that can be employed in combination with a compound of Formula I are disclosed in "Patent focus on new anti-obesity agents," *Exp. Opin. Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Opin. Ther. Patents,* 11: 1677-1692 (2001). The role of neuropeptide Y in obesity is discussed in *Exp. Opin. Invest. Drugs,* 9: 1327-1346 (2000). Cannabinoid receptor ligands are discussed in *Exp. Opin. Invest. Drugs,* 9: 1553-1571 (2000). Various pharmacological approaches for the treatment of obesity is discussed in J-A Fernandez-Lopez, *Drugs:* 62: 915-944 (2002); in H. Bays, et al., "Anti-obesity drug development," *Exp. Opin. Invest. Drugs,* 11: 1189-1204 (2002); and in D. Spanswick, et al., "Emerging Anti-obesity Drugs," *Exp. Opin. Emerging Drugs,* 8(1): 217-237 (2003).

Examples of other active ingredients that may be combined with a compound of Formula I for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R, 12aR)-2,3,6,7,12,12a-hexahydro-2-methyl-6-(3,4-methylenedioxyphenyl)-pyrazino[2',1':6,1]pyrido[3,4-b]indole-1,4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

The instant invention also includes administration of a single pharmaceutical dosage formulation which contains both the MC-4R agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly.

Administration in these various ways are suitable for the present compositions as long as the beneficial pharmaceutical effect of the combination of the MC-4R agonist and the second active ingredient is realized by the subject at substantially the same time. Such beneficial effect is preferably achieved when the target blood level concentrations of each active ingredient are maintained at substantially the same time. It is preferred that the combination of the MC-4R agonist and the second active ingredient be co-administered concurrently on a once-a-day dosing schedule; however, varying dosing schedules, such as the MC-4R agonist once a day and the second active ingredient once, twice or more times per day, is also encompassed herein. A single oral dosage formulation comprised of both a MC-4R agonist and a second active ingredient is preferred. A single dosage formulation will provide convenience for the subject, which is an important consideration especially for subjects with diabetes or obese subjects who may be in need of multiple medications.

The above combinations include combinations of a composition of the present invention not only with one other active compound, but also with two or more other active compounds. Non-limiting examples include combinations of the compositions of the present invention with one, two or more active compounds selected from lipid-lowering agents, and anti-hypertensive agents. Combinations of the compositions of the present invention with one, two or more active compounds selected from lipid lowering agents, and anti-diabetic agents are useful to treat, control or prevent metabolic syndrome. In particular, compositions comprising an anti-obesity agent, such as a melanocortin-4 receptor agonist, an anti-hypertensive agent, in addition to an anti-diabetic agent and/or a lipid lowering agent will be useful to synergistically treat, control or prevent metabolic syndrome.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the melanocortin-4 receptor agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form.

In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Based on their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of structural formula I of the present invention can be prepared according to the procedures of the following Schemes and Examples, using appropriate materials and are further exemplified by the following specific examples. Moreover, by utilizing the procedures described in detail in PCT International Application Publications WO 02/068387 (6 Sep. 2002) and WO 002/068388 (6 Sep. 2002), which are incorporated by reference herein in their entirety, in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention:

BOC (boc) is t-butyloxycarbonyl, BOP is benzotriazol-1-yloxytris(dimethyl-amino)phosphonium hexafluorophosphate, Bu is butyl, calc. is calculated, CBZ (Cbz) is benzyloxycarbonyl, c-hex is cyclohexyl, c-pen is cyclopentyl, c-pro is cyclopropyl, DEAD is diethyl azodicarboxylate, DIEA is diisopropylethylamine, DIPEA is N,N-diisopropylethylamine, DMAP is 4-dimethylaminopyridine, DMF is N,N-dimethylformamide, DMSO is dimethylsulfoxide, EDC is 1-(3-dimethyl-aminopropyl)-3-ethylcarbodiimide HCl, eq. is equivalent(s), ES-MS is electron spray ion-mass spectroscopy, Et is ethyl, EtOAc is ethyl acetate, HATU is O-(7-azabenzotriazol-1-yl)-1,1,3,3-tetramethyluronium hexafluoro-phosphate, HOAt is 1-hydroxy-7-azabenzotriazole, HOBt is 1-hydroxybenzotriazole hydrate, HPLC is high performance liquid chromatography, hr(s) is hour(s); IPA is isopropyl alcohol; LiHMDS is lithium hexamethyl disilazane, LDA is lithium diisopropylamide, MC-xR is melanocortin receptor (x being a number), Me is methyl, MF is molecular formula, MPLC is medium pressure liquid chromatography, MS is mass spectrum, Ms is methanesulfonyl, MTBE is tert-butyl methyl ether, NMM is N-methylmorpholine, OTf is trifluoromethane-sulfonyl, Ph is phenyl, Phe is phenylalanine, Pr is propyl, prep. is prepared, PyBOP is benzotriazol-1-yloxytripyrrolidine phosphonium hexafluorophosphate, r.t. is room temperature, (S)-2-methyl-CBS-oxazaborolidine is (S)-tetrahydro-1-methyl-3,3-diphenyl-1H,3H-pyrrolo[1,2-c][1,3,2]oxazaborole, TEA is triethylamine, TFA is trifluoroacetic acid, TEF is tetrahydrofuran, and TLC or tlc is thin-layer chromatography.

Reaction Schemes A-F illustrate methods employed in the synthesis of the compounds of the present invention of structural formula I. All substituents are as defined above unless indicated otherwise.

Reaction Scheme A illustrates a key step in the synthesis of the novel compounds of structural formula I of the present invention. As shown in reaction Scheme A, the reaction of a piperidine derivative of type 1 with a carboxylic acid derivative of formula 2 affords a title compound of structural formula I. The amide bond coupling reaction illustrated in reaction Scheme A is conducted in an appropriate inert solvent such as methylene chloride or the like and may be performed with a variety of reagents suitable for amide coupling reactions such as EDC, HATU, or PyBOP. Preferred conditions for the amide bond coupling reaction shown in reaction Scheme A are known to those skilled in organic synthesis. Modifications of these reaction conditions may include, but are not limited to, the use of basic reagents such as NMM, TEA, or DIPEA, or the addition of an additive such as HOAt or HOBt. Alternatively, 4-substituted piperidines of formula I may be treated with an active ester or acid chloride derived from carboxylic acid 2 which also affords compounds of structural formula I. The amide bond coupling shown in reaction Scheme A is usually conducted at a temperature between 0° C. and room temperature, occasionally at elevated temperatures, and the coupling reaction is typically conducted for periods of 1 to 24 hours.

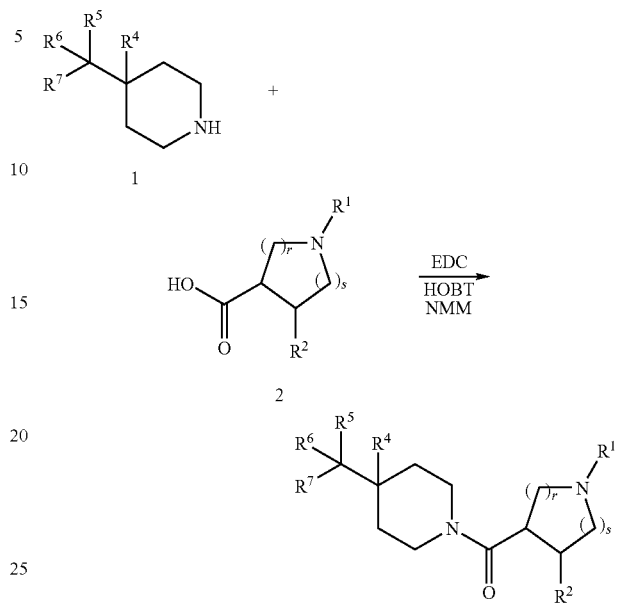

The synthesis of carboxylic acids of general formula 2 utilized in the amide bond coupling reaction in Scheme A was previously described in WO 02/068387 (6 Sep. 2002) and WO 02/068388 (6 Sep. 2002). Reaction Schemes B-F illustrate methods for the synthesis of the carboxylic acids of general formula 2 that are utilized in the amide bond coupling reaction shown in reaction Scheme A. These schemes also feature methods for modification or elaboration of compounds of general formula I.

Reaction Scheme B illustrates a strategy for the synthesis of compounds of general formula 2 wherein the values of r and s are selected such that the resulting heterocycle is a 3-aryl-4-pyrrolidine carboxylic acid derivative 8. The preferred method for the synthesis of compounds of general formula 8 involves the azomethine ylid 3+2 cycloaddition reaction of an azomethine ylid precursor of general formula 4 and a substituted cinnamic ester 3. The azomethine cycloaddition reaction of 3 and 4 affords the 3,4-disubstituted pyrrolidine 5, and the stereochemical relationship of the substituents on the newly formed pyrrolidine ring is determined by the stereochemistry of the double bond in the cinnamate ester 3. Thus the trans ester 3 affords a trans 3,4-disubstituted pyrrolidine of formula 5. The corresponding cis cinnamate ester affords a cis 3,4-disubstituted pyrrolidine of general formula 5. Cis or trans 3-arylpyrrolidine-4-carboxylic esters of general formula 5 may be resolved to afford enantiomerically pure compounds using a method such as resolution by crystallization of the diastereoisomeric salts derived from 5 and a chiral carboxylic acid, or directly by the use of chiral stationary phase liquid chromatography columns. Reaction Scheme B illustrates the case where a trans cinnamnic ester 3 is converted to a trans 3,4-disubstituted pyrrolidine 5 and its subsequent resolution affords the enantiomerically pure trans pyrrolidine esters 6 and 7. Finally, the esters of general formula 5 (or their pure enantiomers 6 and 7) are hydrolyzed to the corresponding amino acid hydrochlorides of general formula 8 as shown at the bottom of reaction Scheme B.

Amino acids of general formula 8 are zwitterionic. Therefore it is in some cases difficult to achieve efficient separation and purification of these compounds from aqueous reactions or workups. In these cases it is preferred to effect the hydrolysis using a reagent such potassium trimethylsilanolate in diethyl ether. Under these conditions the potassium salt of the carboxylic acid is produced which affords an easily isolated precipitate in ether. The resulting salt is then converted to the corresponding amino acid hydrochloride by treatment with excess hydrogen chloride in a suitable solvent such as ethyl acetate. Alternatively, esters such as 5 may be converted directly to the amino acid hydrochlorides 8 under acidic hydrolysis conditions. The hydrolysis of the ester 5 is achieved by prolonged reaction with concentrated hydrochloric acid at an elevated temperature. For example, this reaction may be conducted in 8 M hydrochloric acid at reflux overnight. The reaction mixture is then cooled and evaporated in vacuo to afford the amino acid hydrochloride 8. The amino acid hydrochlorides of general formula 8 correspond to an amino acid hydrochloride of general formula 2 wherein both r and s are 1 and may be employed directly in the amide bond coupling step illustrated in reaction Scheme A to produce the compounds of the present invention of structural formula I.

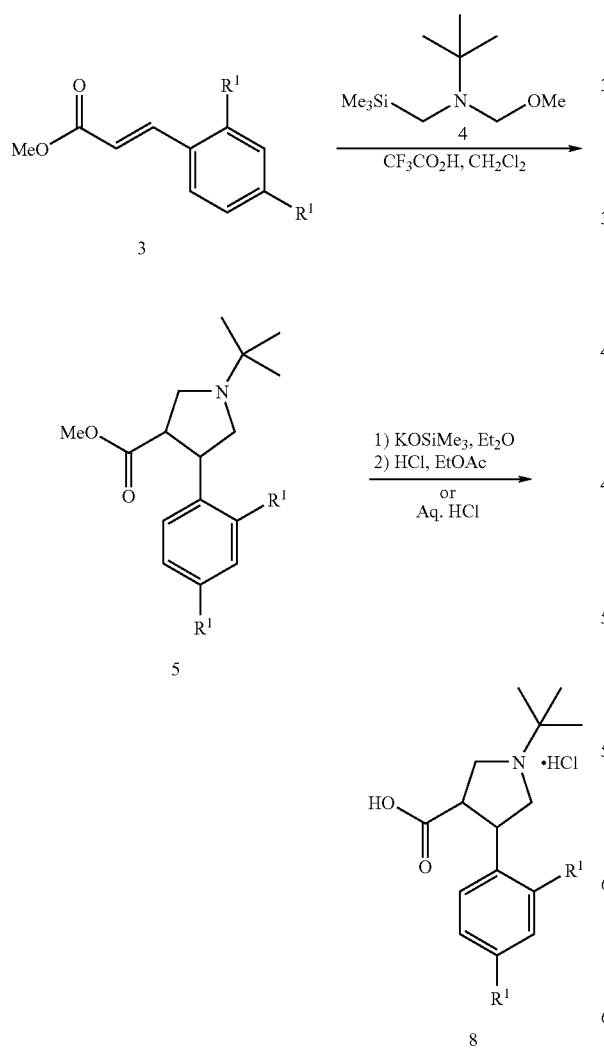

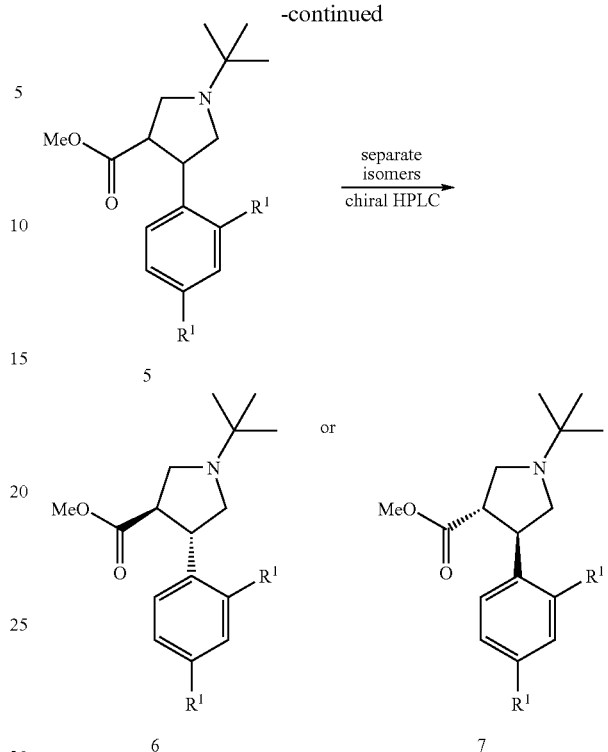

Scheme C illustrates the preparation of azomethine precursors of formula 4 starting with amines of general formula 9. Reaction of the amine of formula 9 with chloromethyltrimethylsilane at high temperature and in the absence of solvent affords the N-trimethylsilylmethyl-substituted amine of general formula 10. Subsequent reaction of 10 with aqueous formaldehyde in the presence of methanol and a base such as potassium carbonate then affords the generalized ylid precursor 4 which can be utilized in the cycloaddition reactions discussed above.

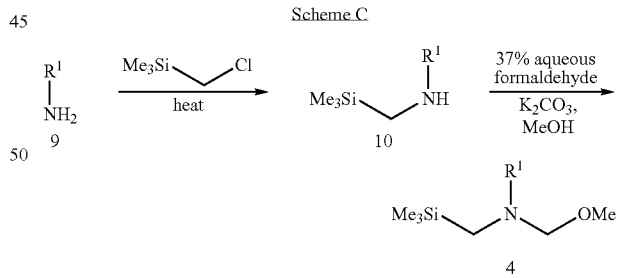

When it is desired to prepare individual enantiomers of the novel title compounds of structural formula I, it is possible to perform a resolution of the compounds of structural formula I using one of the methods known in the art of organic synthesis. For instance, enantiomerically pure compounds (I) may be prepared by crystallization of diastereoisomeric salts formed from the racemic compounds of structural formula I and an optically active carboxylic acid. The two diastereoisomeric salts are separated from each other by fractional crystallization, then the enantiomerically pure compounds of structural formula I are regenerated by treatment of the purified salts with a base. Alternatively, racemic compounds of structural formula I may be resolved by preparative HPLC using commercially available chiral stationary phase columns. Another strategy for the preparation of enantiomerically pure compounds of structural formula I involves preparing enantiomerically pure compounds of general formula 2 prior to their use in the amide bond forming reaction outlined in reaction Scheme A. Racemic compounds of general formula 2, or intermediates used to prepare compounds of formula 2 as described in the previous reaction Schemes (i.e. acid 8, or ester 5) may also be resolved using the classical methods previously discussed.

Scheme D illustrates a strategy for the synthesis of compounds of general formula 2 wherein r is 1 or 2 and s is 1. The synthesis involves the stereoselective reduction of the ketone of compound 11 to give the alcohol 12, and the displacement of the chloride with tert-butyl amine to give compound 13. The nitrogen may then be alkylated via a Michael addition to acrylonitrile, or via reaction with a leaving group substituted alkyl nitrile, such as a bromo butyro nitrile or a bromo propionitrile to give compound 14. Compound 14 is then cyclized to give compound 15, and the nitrile of compound 15 may be hydrolyzed to give the pyrrolidine acid 16.

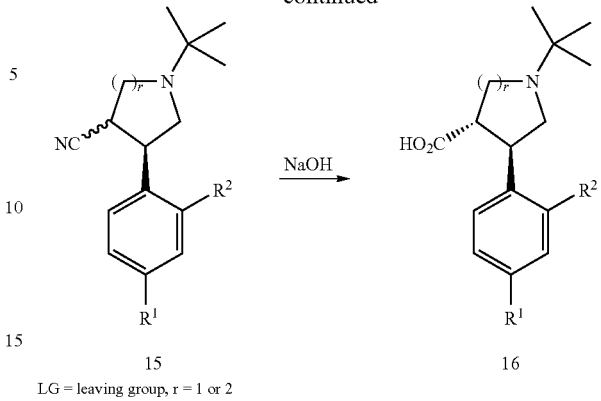

LG = leaving group, r = 1 or 2

Alternatively, the nitrile of compound 15 may be converted to pyrrolidine acid 16 by conversion of nitrile 15 to amide 17, followed by methyl ester 18, as shown in Scheme E.

Scheme D

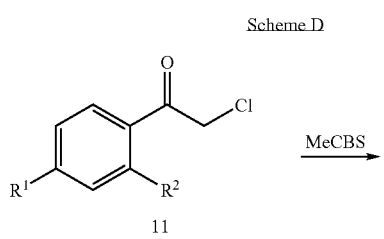

11

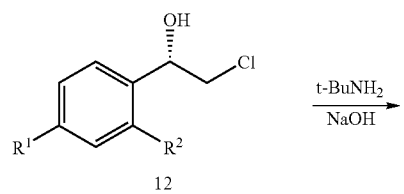

12

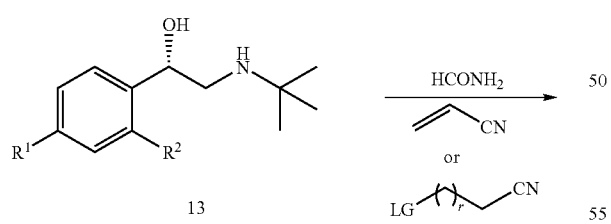

13

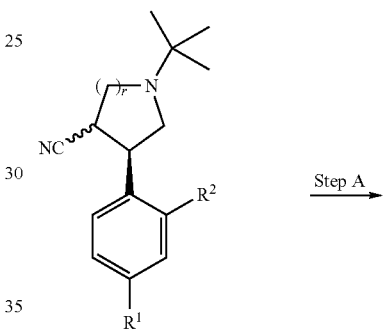

14

Scheme E

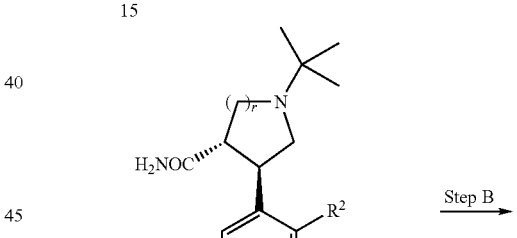

15

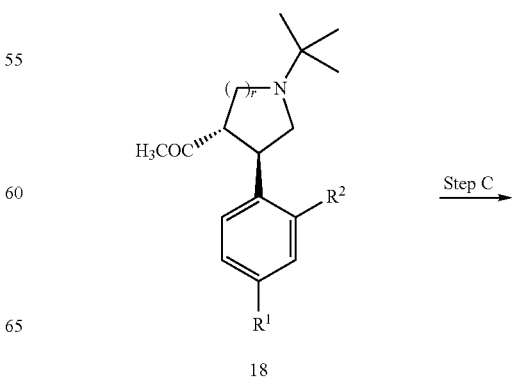

17

18

Reaction Schemes F, G and H illustrate preferred methods for the synthesis of alkyl piperdine intermediates useful to prepare compounds of structural formula I.
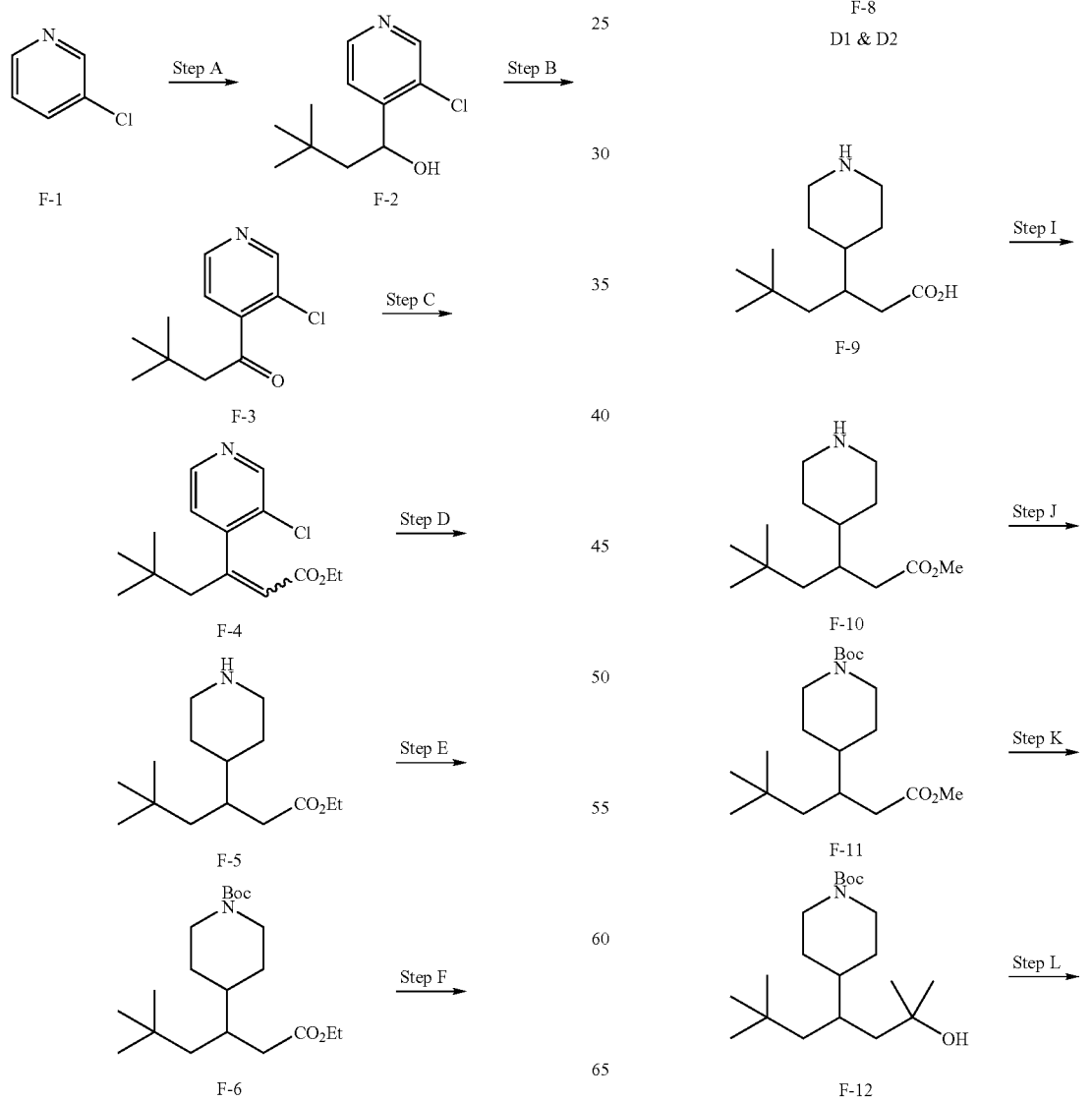

-continued

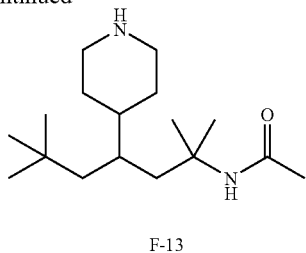

F-13

Step A

To a solution of 3-chloropyridine (F-1, 4.54 g, 40 mmol) in THF (40 ml) at −78° was added slowly a solution of LDA (2M, 20 ml, 40 mmol) in 15 minutes. After stirring the reaction mixture for 20 minutes at −78°, a solution of 3,3-dimethylbutanal (4.0 g, 40 mmol) in THF (51 ml) was added dropwise over ~10 minutes. The reaction mixture was stirred further at −78° for 1 hr, warmed to room temperature, and quenched with aqueous $NaHCO_3$. The mixture was extracted with ethyl acetate, washed with brine, dried and concentrated to give F-2, which was used without further purification in the next step. ES-MS: Calcd. For $C_{11}H_{16}ClNO$: 213. Found 214 ($M^+$+1).

Step B

To a solution of F-2 (8.45 g, 39.6 mmol) in methylene chloride (50 ml) was added 4 Å molecular sieves (4 g), 4-methylmorpholine N-oxide (6.96 g, 59.5 mmol) and tetrapropylammonium perruthenate (694 mg, 1.98 mmol). After stirring the reaction mixture overnight at room temperature, the mixture was diluted with hexane and filtered through a silica gel plug. The silica gel plug was washed with 3:1 hexane/methylene chloride and combined extract was concentrated to give ketone F-3, which was used as such for further reaction. ES-MS: Calcd. For $C_{11}H_{14}ClNO$: 211. Found 212 ($M^+$+1).

Step C

To a solution of F-3 in THF (100 ml) was added 4A molecular sieves (5 g), $LiOH \cdot H_2O$ (3.35 g, 80 mmol) and triethyl phosphonoacetate (17.93 g, 80 mmol). After stirring the reaction mixture at room temperature for 2 days, mixture was filtered and the residue washed with ethyl acetate. The combined organic extracts were washed with brine, dried, concentrated and purified by chromatography over silica gel using 10% ethyl acetate in hexane to give F-4. ES-MS: Calcd. For $C_{15}H_{20}ClNO_2$: 281. Found 282 ($M^+$+1).

Step D

To a solution of F-4 in acetic acid (50 nil) was added platinum oxide (750 mg) and the mixture was stirred at 80° under hydrogen atmosphere overnight. The reaction vessel was flushed with nitrogen, and the mixture filtered and concentrated to give F-5. ES-MS: Calcd. For $C_{15}H_{29}NO_2$: 255. Found 256 ($M^+$+1).

Step E

To a solution of F-5 (7.1 g, 22.53 mmol) in methylene chloride (75 ml) was added triethyl amine (6.8 g, 67.59 mmol) and di t-butyl dicarbonate (4.91 mmol). After stirring the reaction mixture for 4 hr at room temperature, mixture was diluted with methylene chloride, washed with water, dried and concentrated to give F-6. ES-MS: Calcd. For $C_{20}H_{37}NO_4$: 355. Found 356 ($M^+$+1).

Step F

To a solution of F-6 (7.5 g, 21.26 mmol) in ethanol (50 ml) was added a solution of $LiOH \cdot H_2O$ (3.54 g, 84.5 mmol) in water (30 ml). After stirring the reaction mixture at room temperature overnight, the mixture was concentrated, acidified and partitioned between ethyl acetate and water. The organic layer was dried and concentrated to give F-7. ES-MS: Calcd. For $C_{18}H_{33}NO_4$: 327. Found 328 ($M^+$+1).

Step G

To a solution of F-7 (4.7 g, 14.37 mmol) in methylene chloride (40 ml) was added EDC (4.82 g, 25.15 mmol), HOBT (3.39 g, 25.15 mmol), NMM (4.37 g, 43.11 mmol) and (1S)-phenylethylamine (1.74 g, 14.37 mmol). After stirring the reaction mixture at room temperature overnight, the mixture was diluted with methylene chloride, washed with water, aqueous HCl, dried and concentrated. The resulting residue was chromatographed over silica gel using 4% t-butyl methyl ether in methylene chloride to give F-8 D1 and F-8 D2. ES-MS: Calcd. For $C_{26}H_{42}N_2O_3$: 430. Found 431 ($M^+$+1).

Step H

A solution of F-8 (D1, 1.73 g, 4.02 mmol) in concentrated HCl (15 ml) was heated in a sealed tube at 130° overnight. The reaction mixture was cooled and concentrated to give F-9 as a white solid, which was used in the next step without further purification. ES-MS: Calcd. For $C_{13}H_{25}NO_2$: 227; Found 228 ($M^+$+1).

Step I

To a solution of F-10 (913 mg, 4.02 mmol) in methanol (30 ml) was added 5 ml of 4N HCl in dioxane. After stirring the reaction mixture for overnight at room temperature, mixture was concentrated to give F-10. ES-MS: Calcd. For $C_{14}H_{27}NO_2$: 241. Found 242 ($M^+$+1).

Step J

To a solution of F-10 (1.1 g, 4.03 mmol) in methylene chloride was added triethylamine (1.938 g, 1916 mmol) and di tert-butyl dicarbonate (1.046 g, 4.8 mmol). After stirring the reaction mixture for over night, reaction was diluted with methylene chloride, washed with water, dried and concentrated to give F-11. ES-MS: Calcd. For $C_{19}H_{35}NO_4$: 341. Found 342 ($M^+$+1).

Step K

To a solution of F-11 (1.36 g, 4.0 mmol) in THF (15 ml) at 0° C. was added dropwise MeMgBr (3M, 4.66 ml, 14 mmol) over ~10 minutes. The reaction mixture was warmed to room temperature and stirred overnight. The reaction was quenched with aqueous $NaHCO_3$, extracted with ethyl acetate, dried and concentrated to give F-12, which was used in the next step without further purification. ES-MS: Calcd. For $C_{20}H_{39}NO_3$: 341. Found 364 ($M^+$+23).

Step L

To a solution of F-12 (1.35 g, 3.95 mmol) in $CH_3CN$ (15 ml) at 0° C. was added concentrated $H_2SO_4$ (1.759 ml, 31.65 mmol). The reaction mixture was warmed to room temperature and stirred for 2 days. Then the mixture was basified with 5N NaOH (15 ml), concentrated and extracted with ethyl acetate. The organic layer was dried and concentrated to give crude F-13. ES-MS: Calcd. For $C_{17}H_{34}N_2O$: 282. Found 283 ($M^+$+1).

Following the synthetic route described in Scheme F and using the appropriate reagents, the following intermediates were prepared:
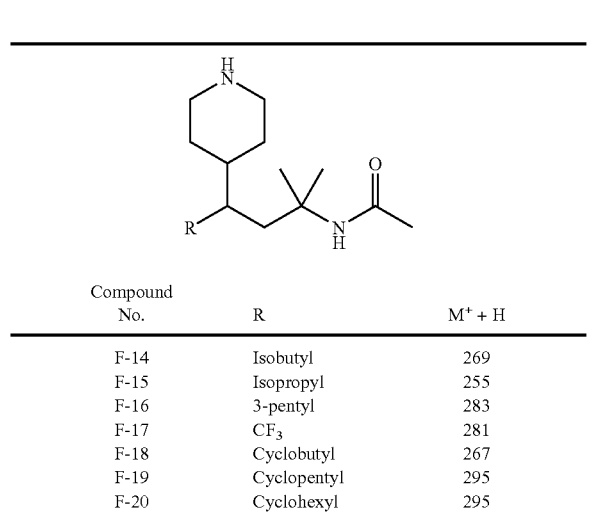
| Compound No. | R | M⁺ + H |
|---|---|---|
| F-14 | Isobutyl | 269 |
| F-15 | Isopropyl | 255 |
| F-16 | 3-pentyl | 283 |
| F-17 | $CF_3$ | 281 |
| F-18 | Cyclobutyl | 267 |
| F-19 | Cyclopentyl | 295 |
| F-20 | Cyclohexyl | 295 |
Scheme G
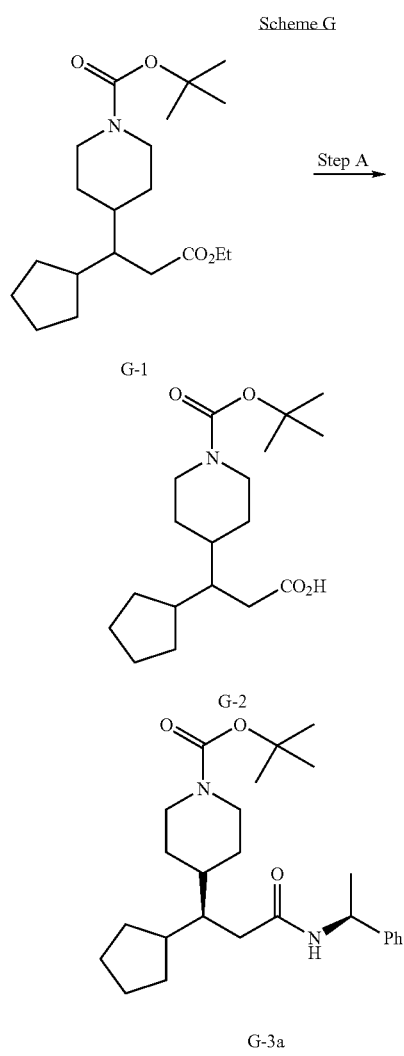
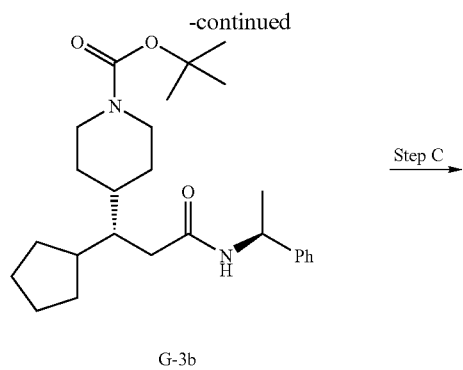
G-3b
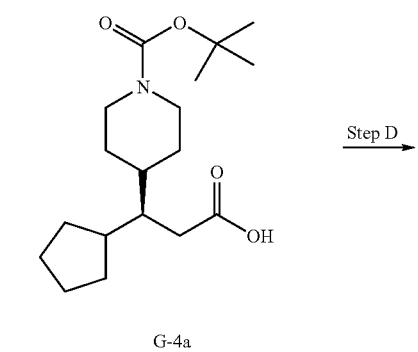
G-4a
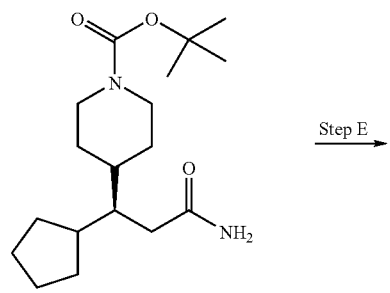
G-5a
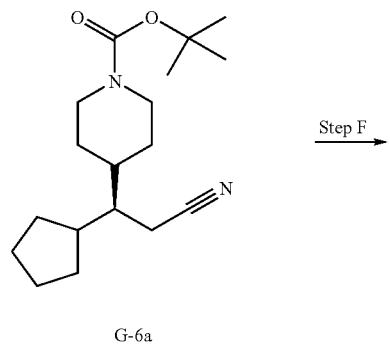
G-6a

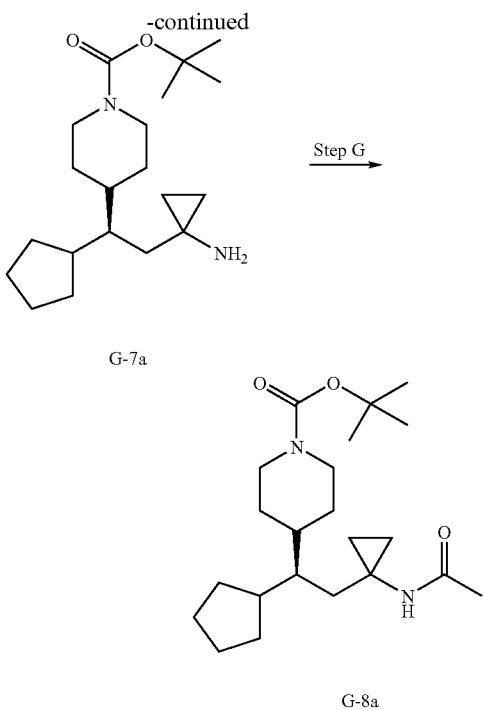

G-7a

G-8a

Step A:

Preparation of 3-[1-(tert-butoxycarbonyl)piperidin-4-yl]-3-cyclopentyl-propanoic acid (G-2)

A solution of 5N aqueous NaOH (41.7 ml, 208.50 mmol) was added in one portion to a solution of ester G-1 (18.40 g, 52.05 mmol) in ethanol (163 mL) and water (65 mL). The resulting solution was heated to reflux and refluxed for 1.5 h, then cooled to room temperature and stirred overnight. The ethanol was removed in vacuo and the resulting residue was diluted with water and washed once with ether to give three layers. The uppermost ether layer was separated and discarded, and the remaining two layers were collected and acidified with 2N HCl (110 mL). The mixture was extracted three times with ethyl acetate. The combined organic extracts were washed with brine, dried over MgSO$_4$, filtered and the filtrate concentrated in vacuo giving the acid G-2 as a clear viscous oil. ES-MS Calculated for $C_{18}H_{31}NO_4$: 325.5. Found: $[M+H]^+=326.4$.

Step B:

Preparation of tert-butyl 4-((1S)-1-cyclopentyl-3-oxo-3-{[(1S)-1-phenethyl]amino}propyl)piperidine-1-carboxylate (G-3a) and tert-butyl 4-((1R)-1-cyclopentyl-3-oxo-3-{[(1S)-1-phenethyl]amino}propyl) piperidine-1-carboxylate (G-3b)

1-Hydroxybenzotriazole hydrate (9.01 g, 58.85 mmol) was added to a solution of acid G-2 (15.97 g, 49.06 mmol) in methylene chloride (160.0 mL) followed by addition of EDC (14.11 g, 73.60 mmol) in one portion. The suspension was stirred at ambient temperature until all solids dissolved (~10-15 min), then (S)-(-)-alpha-methylbenzylamine (7.50 mL, 58.91 mmol) was added dropwise from a syringe over 5 min resulting in a slight exotherm. The reaction mixture was stirred overnight at ambient temperature. The solvent was evaporated in vacuo, replaced with ethyl acetate and the solution washed one time each with water, 2N HCl, saturated aqueous sodium bicarbonate and brine. The organic layer was separated and dried over MgSO$_4$, filtered, evaporated to dryness in vacuo and dried under vacuum to give a mixture of 3a and 3b as a foam. The diastereomers were separated by flash chromatography on silica gel (4% methyl t-butyl methyl ether/dichloromethane) to give G-3a and G-3b. Mixture fractions were re-chromatographed affording additional amounts of pure diastereomers. ES-MS Calculated for $C_{26}H_{40}N_2O_3$: 428.6. Found: $[M+Na]^+=451.4$.

Step C:

Preparation of (3S)-3-[1-(tert-butoxycarbonyl)piperidin-4-yl]-3-cyclopentylpropanoic acid (G-4a)

Amide G-3a (1.71 g, 3.99 mmol) was placed in a thick-walled threaded tube with concentrated HCl (30.0 mL) and a magnetic stirring bar and sealed with a threaded Teflon stopper and O-ring. The sealed tube was heated with stirring at 130° C. for a total of 16.5 h and then cooled in an ice bath before opening the tube. The reaction mixture was washed twice with ether and then concentrated in vacuo. Toluene was added to the residue and the resulting solution evaporated to dryness and dried briefly under vacuum. The residue was dissolved in a 1:1 solution of THF/ater (24.0 mL) and sodium bicarbonate (1.20 g, 14.29 mmol) was carefully added. The solution was stirred for approximately 10 min after which BOC anhydride (1.05 g, 4.81 mmol) was added in one portion. The reaction was stirred overnight, then acidified by addition of 1N HCl (11.0 mL). The layers were separated, and the aqueous layer was extracted twice with ethyl acetate. The combined organic layers were washed three times with brine, dried over MgSO$_4$, filtered and the filtrate evaporated in vacuo giving resolved acid G-4a as a viscous oil. Crude G-4a was used without further purification. ES-MS Calculated for $C_{18}H_{31}NO_4$: 325.5. Found: $[M+H]^+=326.4$.

Step D:

Preparation of tert-butyl 4-[(1S)-3 amino-1-cyclopentyl-3-oxopropyl]-piperidine-1-carboxylate (G-5a)

1-Hydroxybenzotriazole hydrate (368 mg, 2.40 mmol) and EDC (461 mg, 2.40 mmol) were added in one portion to a solution of acid G-4a (430 mg, 1.20 mmol) in acetonitrile. The mixture was stirred for 1 h at ambient temperature, then a 2N solution of ammonia in methanol (2.4 mL, 4.8 mmol) was added. The reaction mixture was stirred for 2.5 h, then the solvent was evaporated and replaced with ethyl acetate. The solution was washed with water, 2N HCl, saturated aqueous NaHCO$_3$ and brine, dried over MgSO$_4$, filtered and the filtrate evaporated in vacuo. Brief drying under vacuum yielded amide G-5a as an amorphous foam, which was used without further purification. ES-MS Calculated for $C_{18}H_{32}N_2O_3$: 324.5. Found: $[M+H]^+=325.5$.

Step E:

Preparation of tert-butyl 4-[(1S)-2-cyano-1-cyclopentylethyl]piperidine-1-carboxylate (G-6a)

Trifluoroacetic anhydride (1.0 mL) was added dropwise from a syringe over 5 min to a solution of G-5a (350 mg, 1.08 mmol) in pyridine (1.0 mL). The addition resulted in a mild exotherm and solids precipitated to give a thick yellow paste which was stirred for 15 min. Ether (5 mL) was added and stirring was continued for an additional 20 min. Water (10 mL) was added to dissolve the solids and the layers were separated. The aqueous layer was extracted twice with ether and the combined organic extracts washed with water, 2N HCl, saturated aqueous NaHCO$_3$ and brine, dried over MgSO$_4$, filtered and the filtrate was evaporated in vacuo. Drying under vacuum gave G-6a as a viscous yellow oil, which was used without further purification. ES-MS: Calculated for C$_{18}$H$_{30}$N$_2$O$_2$: 306.5. Found: [M+Na]$^+$=329.3.

Step F:

Preparation of tert-butyl 4-[(1S)-2-(1-aminocyclopropyl)-1-cyclopentylethyl] piperidine-1-carboxylate (G-7a)

Titanium (IV) isopropoxide (336.0 µL, 1.14 mmol) was added to a solution of nitrile G-6a (268 mg, 0.87 mmol) in THF (5.0 mL) and the resulting solution was cooled to −70° C. A solution of ethylmagnesium bromide in THF (1M, 2.34 mL, 2.34 mmol) was added from a syringe over several minutes. The clear bright yellow solution was stirred at −70° C. for ten min and then warmed to ambient temperature and stirred for 1 h. Boron trifluoride diethyl etherate (270 µL, 2.13 mmol) was added and the dark brown solution was stirred for 1 h longer. 1N HCl (2.82 mL) was added and after stirring for 5 min the reaction mixture was basified with 10% aqueous KOH (10.0 mL). The mixture was then filtered through Celite® filtering aid and the layers from the filtrate separated. The aqueous layer was extracted twice with ethyl acetate and the combined organic layers were washed once with brine. The organic layer was dried over MgSO$_4$, filtered, and the filtrate was evaporated to dryness. Purification by flash chromatography on silica gel (hexane/ethyl acetate/methanol, 12:8:2) gave the amino cyclopropane G-7a as a viscous colorless oil and unreacted nitrile G-6a was also recovered. ES-MS: Calculated for C$_{20}$H$_{36}$N$_2$O$_2$: 336.5. Found: [M+H]$^+$= 337.4.

Step G:

Preparation of tert-butyl 4-{(1S)-2-[1-(acetylamino)cyclopropyl]-1-cyclopentylethyl}piperidine-1-carboxylate (G-8a)

Acetic anhydride (36 µL, 0.38 mmol) was added to a solution of amino cyclopropane G-7a (116 mg, 0.34 mmol) and N,N-diisopropylethylamine (72 µL, 0.41 mmol) in dichloromethane (5 mL) and stirred at ambient temperature for 1 h and 15 min. The solvent was evaporated and replaced with ethyl acetate, washed with water, 2N HCl, saturated aqueous NaHCO$_3$ and brine, dried over MgSO$_4$, filtered, and the filtrate was evaporated in vacuo. Drying under vacuum gave the acetylated amino cyclopropane G-8a as an amorphous foam, which was used without further purification. ES-MS: Calculated for C$_{22}$H$_{38}$N$_2$O$_3$: 378.6. Found: [M+H]$^+$=379.5.

Scheme H

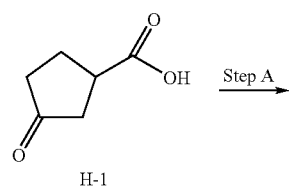

H-1

Step A

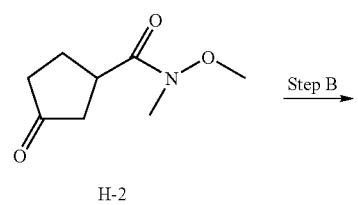

H-2

Step B

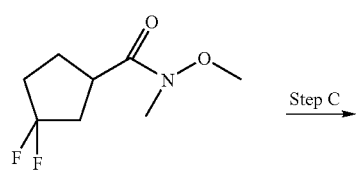

H-3

Step C

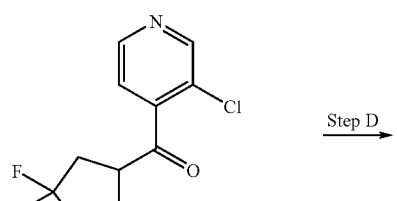

H-4

Step D

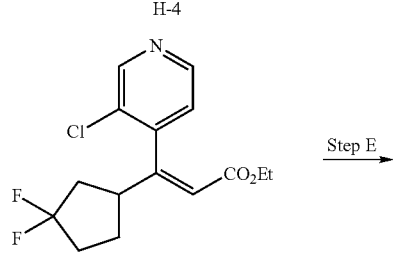

H-5

Step E

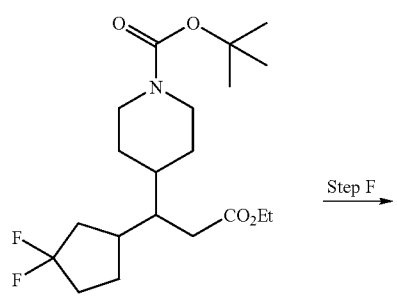

H-6

Step F

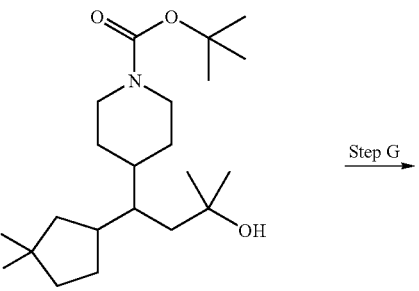

H-7

Step G

-continued

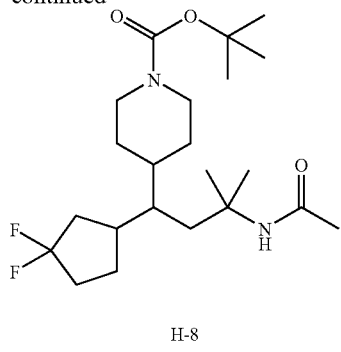

H-8

Starting material 3-oxocyclopentanecarboxylic acid (H-1) was prepared following literature procedures (J. Chem. Soc., 1912, 101, 892).

Step A:

Preparation of
N-methoxy-N-methyl-3-oxocyclopentanecarboxamide
(H-2)

N,O-dimethylhydroxylamine hydrochloride (8.02 g, 82.17 mmol) and triethylamine (11.5 mL, 82.50 mmol) were added to a solution of acid H-1 (97%, 7.38 g, 55.85 mmol), 1-hydroxybenzotriazole hydrate (12.6 g, 82.30 mmol) and EDC (15.76 g, 82.21 mmol) in methylene chloride (70 mL) and stirred overnight at ambient temperature. Evaporated the reaction mixture to dryness and purified the crude product by flash chromatography on silica gel (hexane-ethyl acetate, 1:1) giving the Weinreb amide H-2 as a yellow oil. ES-MS Calculated for $C_8H_{13}NO_3$: 171.2. Found: $[M+H]^+=172.1$.

Step B:

Preparation of 3,3-difluoro-N-methoxy-N-methylcyclopentanecarboxamide (H-3)

Deoxo-Fluoro® (50% in toluene, 15.0 mL, 40.66 mmol) and TFA (230 µL, 3 mmol) were added to a solution of amide H-2 (2.56 g, 14.95 mmol) in toluene (30 mL). The reaction mixture was heated to 40° C. overnight then diluted with ether and cooled in an ice bath. 2N NaOH (75.0 mL) was added with vigorous stirring. The organic layer was separated and the aqueous layer was extracted once with ether. The combined organic layers were washed with brine, dried over $MgSO_4$, decolorized with charcoal, filtered and the filtrate was evaporated in vacuo. The crude product was purified by flash chromatography on silica gel (hexane/ethyl acetate, 1:1) to give the gem difluoro amide H-3 as a light yellow liquid. ES-MS: Calculated for $C_8H_{13}F_2NO_2$: 193.2. Found: $[M+H]^+= 194.1$.

Step C:

Preparation of (3-chloropyridin-4-yl)(3,3-difluorocyclopentyl)methanone (H-4)

LDA (2M in THF/n-heptane, 6.35 mL, 12.70 mmol) was added dropwise from a syringe over 10 min to a solution of 3-chloropyridine (1.21 mL, 12.72 mmol) in THF (15.0 mL) at −78° C. and stirred for 0.5 h at that temperature. A solution of difluoro amide H-3 (1.888 g, 9.77 mmol) in THF was added from a syringe over 10 min and the clear orange solution was stirred for 1 h longer at low temperature before warming to ambient temperature. After stirring an additional 15 min the reaction was quenched by the addition of saturated aqueous $NH_4Cl$. Water was added, the layers separated and the aqueous portion extracted twice with ethyl acetate. The combined organic layers were washed with brine, dried over $MgSO_4$, decolorized with charcoal, filtered and the filtrate was evaporated in vacuo. The crude product was purified by flash chromatography on silica gel (hexane/ethyl acetate, 1:1) to give the ketone H-4 as a yellow oil. ES-MS: Calculated for $C_{11}H_{10}ClF_2NO$: 245.2. Found: $[M+H]^+=246.2$.

Step D:

Preparation of ethyl (2Z)-3-(3-chloropyridin-4-yl)-3-(3,3-difluorocyclo-pentyl)acrylate (H-5)

Triethyl phosphonoacetate (1.53 mL, 7.66 mmol) was added neat, dropwise over 5 min to a suspension of sodium hydride (60% oil dispersion washed twice with hexane, 306 mg, 7.66 mmol) in THF (11 mL) resulting in vigorous gas evolution but very little exotherm. The mixture was stirred at ambient temperature until all of the sodium hydride had reacted (about 5 min). A solution of ketone H-4 (1.568 g, 6.38 mmol) in THF (11 mL) was added all at once. The reaction mixture was heated to reflux and refluxed with stirring overnight. The two phase mixture was cooled to ambient temperature, diluted with ethyl acetate and water added to dissolve the oily precipitate. The layers were separated and the aqueous portion extracted twice with ethyl acetate. The combined organic layers were washed with brine, dried over $MgSO_4$, filtered and the filtrate was evaporated in vacuo. The crude product was purified by flash chromatography on silica gel (hexane/ethyl acetate, 1:1) to give the acrylate H-5 as a light yellow oil, primarily as the Z isomer. ES-MS: Calculated for $C_{15}H_{16}ClF_2NO_2$: 315.3. Found: $[M+H]^+=316.1$.

Step E:

Preparation of tert-butyl 4-[1-(3,3-difluorocyclopentyl)-3-ethoxy-3-oxopropyl]piperidine-1-carboxylate (H-6)

Platinum (IV) oxide (60 mg) was added to a solution of the acrylate H-5 (290 mg, 0.92 mmol) in acetic acid (5 mL), the mixture heated to 50° C. with stirring and reduced with $H_2$ at atmospheric pressure (balloon) overnight. The reaction mixture was filtered through Celite® filtering aid to remove catalyst and the filtrate was evaporated to dryness in vacuo. The resulting residue was dissolved in a small amount of toluene and evaporated; this process was repeated several times. The residue was dried under vacuum yielding a viscous oil which was then dissolved in methylene chloride (5 mL) and treated with triethylamine (257 µL, 1.84 mmol) and BOC anhydride (221 mg, 1.01 mmol) stirring overnight at ambient temperature. The solvent was evaporated and replaced with ethyl acetate and washed with water, 2N HCl, saturated $NaHCO_3$ and brine, dried over $MgSO_4$, filtered and the filtrate evaporated. The crude product was purified by flash chromatography on silica gel (hexane/ethyl acetate, 3: 1) to give the ester H-6 as a colorless oil. ES-MS: Calculated for $C_{20}H_{33}F_2NO_4$: 389.5. Found: $[M+Na]^+=412.1$.

Step F:

Preparation of tert-butyl 4-[1-(3,3-difluorocyclopentyl)-3-hydroxy-3-methylbutyl]piperidine-1-carboxylate (H-7)

Methylmagnesium chloride (3M in THF, 644 µL, 1.93 mmol) was added to a stirring solution of the ester H-6 (188 mg, 0.48 mmol) in THF (3 mL) at 0° C. and the reaction mixture allowed to warm overnight to ambient temperature. Then 10% acetic acid (10 mL) was added, and the mixture was extracted with ethyl acetate three times filtering through filtercel after the first extraction. The combined organic layers were washed with saturated aqueous NaHCO$_3$ until washes were basic and then washed with brine, dried over MgSO$_4$, filtered and the filtrate was evaporated. The crude product was purified by flash chromatography on silica gel (hexane/ethyl acetate, 2:1) to give the alcohol H-7 as a colorless viscous oil. ES-MS: Calculated for $C_{20}H_{35}F_2NO_3$: 375.5. Found: $[M+H]^+=376.2$.

Step G:

Preparation of tert-butyl 4-[3-(acetylamino)-1-(3,3-difluorocyclopentyl)-3-methylbutl]piperidine-1-carboxylate (H-8)

Concentrated sulfuric acid (212 µL, 3.98 mmol) was added to a solution of the alcohol H-7 (148 mg, 0.394 mmol) in acetonitrile (2.0 mL) which had been cooled to 0° C. The reaction mixture was warmed slowly to ambient temperature and stirred for 48 h. The solvent was evaporated and 5N NaOH (2.2 mL), water, and brine were added to the residue which was then extracted with dicloromethane three times. The combined organic layers were washed with brine, dried over MgSO$_4$, filtered and the filtrate was evaporated in vacuo. The residue was dried under vacuum yielding a colorless oil which was then dissolved in methylene chloride (4 mL) and treated with triethylamine (58 µL, 0.41 mmol) and BOC anhydride (90 mg, 0.41 mmol) stirring for 2 h at ambient temperature. The solvent was evaporated and replaced with ethyl acetate and washed with water, 2N HCl, saturated aqueous NaHCO$_3$ and brine, dried over MgSO$_4$, filtered and the filtrate evaporated. Drying under vacuum gave the acetamide H-8 (85%) which was used without further purification. ES-MS: Calculated for $C_{22}H_{38}F_2N_2O_3$: 416.5. Found: 417.2.

Reaction Schemes I and J illustrate preferred methods for the synthesis of pyrrolidine acid intermediates (I-6, I-7) and piperidine acid intermediates (J-5) useful to prepare compounds of structural formula I.

Scheme I

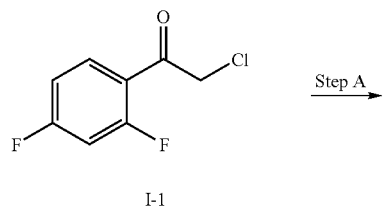

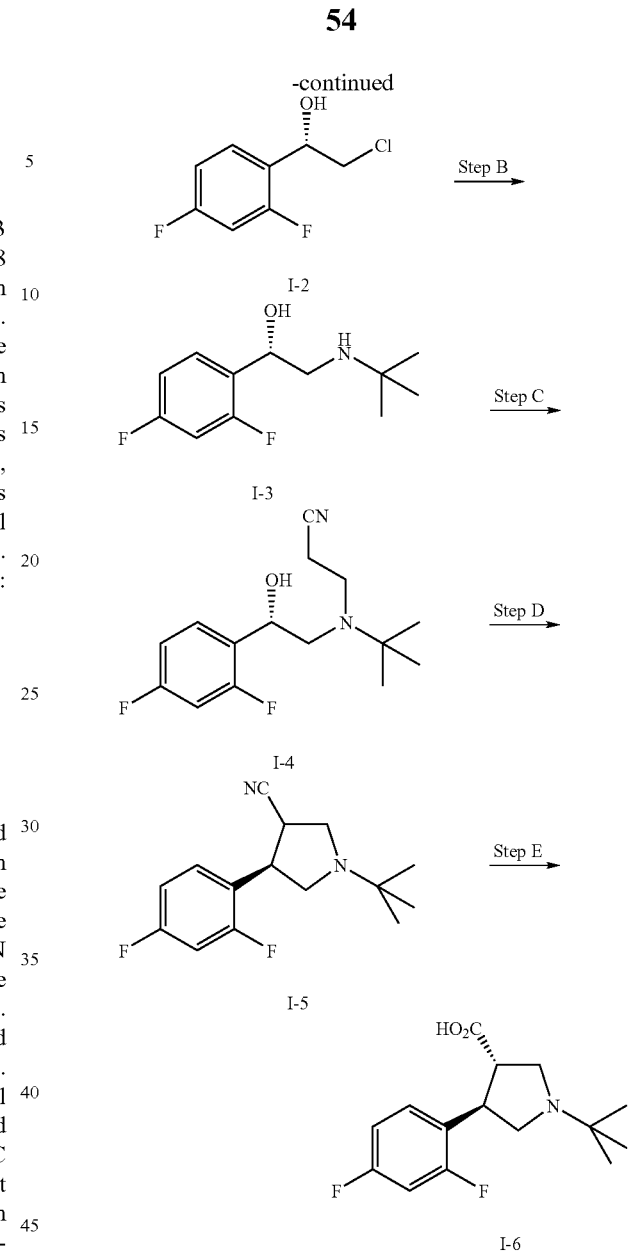

Preparation of Intermediate (3S,4R)-1-tert-butyl-4-(2,4-difluorophenyl)pyrrolidine-3-carboxylic acid I-6

Step A

A solution of (S)-2-methyl-CBS-oxazaborolidine (131 mL, 1 M in toluene), borane-N,N-diethylaniline (46.36 L) in MTBE (10 L) was heated to 38-42° C., then a solution of 2-chloro-2',4'-di-fluoro-acetophenone I-1 (4891 g) in MTBE (16 L) was added over 10 hr. The homogeneous solution was stirred at 40° C. for one hour, then allowed to cooled to 18° C. and stirred overnight. Methanol (2.3 L) was added over 60 min, while maintaining the temperature at <20° C. with cooling. The reaction mixture was stirred 30 min, then 5 N aq HCl (10 L) was added over 30 min, while maintaining the temperature at 22-25° C. with cooling. After stirring 30 min, the phases were separated, and the organic phase was washed with saturated aqueous NaCl, then concentrated in vacuo to obtain a solution of compound I-2.

Step B

Compound I-2 in the MTBE solution from Step A (5040 g, 98 wt %, 25.67 mol) was diluted with methanol (5 L), then tert-butylamine (25 L) was added. The mixture was cooled to 25° C., solid NaOH pellets (1048 g) were added, and the resulting reaction mixture was stirred and warmed to reflux. After 12-20 hr at reflux, the mixture was concentrated in vacuo to ⅓ volume, then water (5 L) and MTBE (20 L) were added. The phases were separated and the aqueous phase was re-extracted with MTBE (2×2 L). The combined extracts were washed with saturated aqueous NaCl (1 L), and then concentrated in vacuo. Heptane (40 L) was added and the concentration was continued to bring the volume to 20 L. The mixture was heated to ~90° C. to dissolve all solids, then allowed to cool to 22° C. to crystallize over 4 hr. The mixture was cooled to 0° C., stirred 12-15 hr, then filtered. The resulting filtrate was washed with cold heptane (2×5 L), then dried in vacuo at 35° C. to obtain compound I-3.

Step C

A mixture of compound I-3 (5.205 kg, 99.9%, 22.68 mol) and acrylonitrile (26.9 L, 408 mol) was heated to reflux (~77° C.) under nitrogen atmosphere. After heating for 20 h (~90% conversion), one equivalent each of ethanol (1.32 L, 22.68 mol) and formamide (0.9 L, 22.68 mol) was added and heating was continued for 12 h. After cooling to 22° C., the solution was concentrated to 12 L by distillation (80-90 torr at 20-22° C. pot temperature), and the resulting residue was diluted with isopropyl acetate (22 L) and re-concentrated (55-75 torr and 22-27° C. pot temperature). This was repeated. Then the residue was diluted with isopropyl acetate to a total volume of 34 L, and the supernatant was filtered using a 10-15 μm porosity filter. The filter cake was washed with isopropyl acetate, and the filtrate was diluted with a total of 24 L of isopropyl acetate. The combined filtrate (~54 L) was washed with a solution made up of water (31.2 L), acetic acid (52 mL, 4 mol %), and saturated brine (3.1 L), followed by a 12% aqueous NaCl wash (2×34 L). The organic layer was concentrated (15-45 torr and 5-29° C.) to ~15 L volume and flushed with 5×6 L n-heptane, during which time product crystallized. The slurry was diluted with n-heptane to a volume of 23 L and stirred at 0-5° C. for 1-3 days until a concentration of 10 g/18 L was achieved, then filtered and washed with cold (5° C.) n-heptane (14 L). The wet cake was dried in vacuo at 20° C. with a nitrogen sweep to afford compound I-4.

Step D

A solution of compound I-4 (5.73 kg, 99.9%, 20.28 mol) in dry THF (31.3 L) was cooled to −20° C., then chloro diethylphosphate (3.79 kg, 21.29 mol) was added. LiHMDS (1.35 M in THF solution; 31.5 L, 42.58 mol) was slowly added over 1.5 h while maintaining the reaction temperature at −15° C. After stirring at −15° C. for 2 h, the reaction mixture was quenched with water (50.6 L) at <15° C. and extracted with n-heptane (40.5 L) at 20° C. The organic layer was washed with 10% aq NaCl solution (52 L), and extracted with 3 N HCl solution (40.6 L, 121.8 mol) with cooling to keep the temperature <35° C. The aqueous layer (58 L) was adjusted to pH 11-12 with 50% aq NaOH (6.13 L, 116.1 mol) and extracted with n-heptane (54 L). The organic phase was washed once with 10% aq NaCl solution (26 L) and the resulting heptane solution containing compound I-5 was used in Step E.

Step E

The solution of compound I-5 (4.88 kg, 18.46 mol) in n-heptane (~65 L total) from the Step D was solvent-switched to ethanol (~20.6 L total). To this solution was added 50% aq NaOH (2.7 L, 51.15 mol) over 2 min with stirring. Upon addition of the NaOH, the temperature of the mixture rose from 16 to 34° C. The mixture was then heated to reflux (78-80° C.) under nitrogen for 5-6 h. After cooling to 20° C., the solution was diluted with ethanol (25.4 L) and methanol (40.6 L). The solution was then cooled to 12° C.; the pH was adjusted to apparent pH 6.8 with 96% H$_2$SO$_4$ (1.42 L, 25.6 mol), while maintaining the temperature at ~20° C. The sodium sulfate slurry was filtered through a bed of Solka-Floc® (5 kg) and anhydrous powder Na$_2$SO$_4$ (4 kg), and washed with 1:1 EtOH:MeOH (20 L). The filtrate was filtered, concentrated and solvent-switched to a 2-propanol solution (~15 L volume). The resulting slurry was heated at reflux (~80° C.) for 2 h, then cooled to 16° C. MTBE (30.4 L, 3 vol relative to IPA) was added to the mixture over 5 h. After stirring at 16-17° C. for 3 days, the resulting slurry was filtered and washed with 12 L 1:3 IPA:MTBE. The solids were dried in vacuo (150 torr) at 50° C. with a nitrogen sweep to give compound I-6.

Following the synthetic route in Scheme I and using the appropriate reagents, (3S,4R)-1-tert-butyl-4-(2-fluoro-4-chlorophenyl)pyrrolidine-3-carboxylic acid 1-7 was prepared:

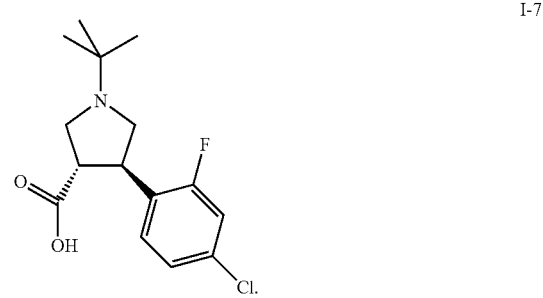

I-7

Scheme J

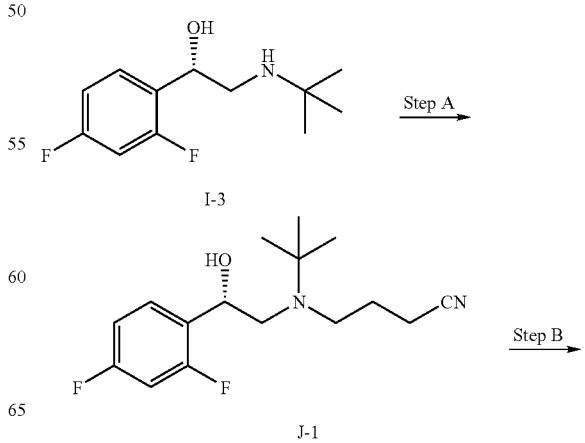

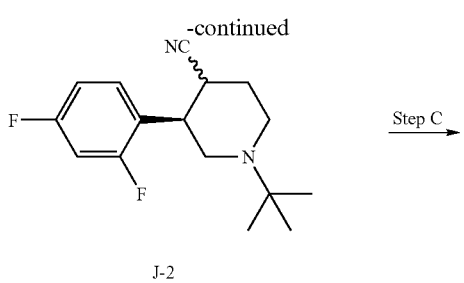

J-2

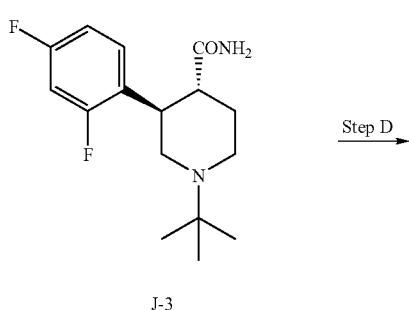

J-3

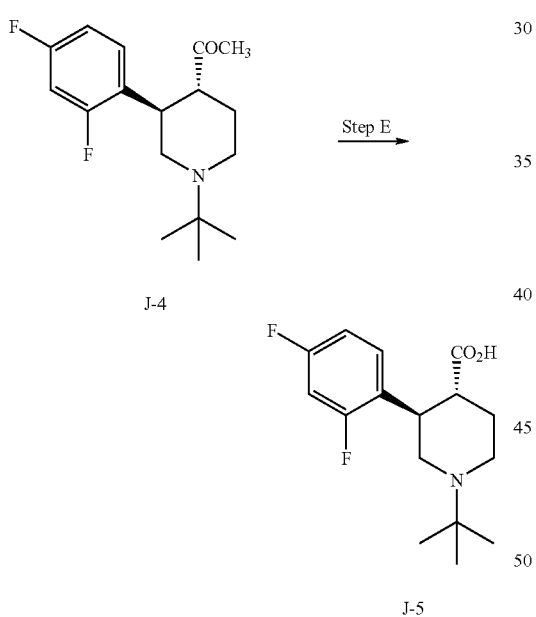

J-4

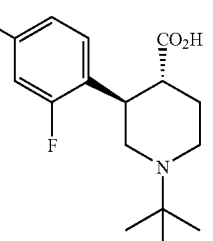

J-5

Preparation of (3R,4R)-1-tert-butyl-3-(2,4-difluorophenyl)piperidine-4-carboxylic acid (J-5)

Step A

A mixture of compound I-3 (24 g, 0.105 mol), 4-bromobutyronitrile (42 g, 0.28 mole, 2.7 eq) $K_2CO_3$ (22 g, 0.16 mol, 1.52 eq) and DMF (70 mL) was heated at 50° C. for 64 hr. The reaction was quenched into water (500 mL) and extracted with ether (2×250 mL). The ether layer was extracted with 1N HCl (2×125 mL), and the resulting aqueous layer was extracted with hexanes (2×100 mL). The aqueous layer was then made basic with 5N NaOH, and extracted with ether (2×250 mL). The organic layer was washed with brine, dried with $Na_2SO_4$, filtered and concentrated. The residue was chromatographed (silica, 9/1 hexanes/THF then 4:1 hexanes/THF) to give compound J-1 as a colorless oil.

Step B

Compound J-1 (50 g, 0.169 mol) was dissolved in TUF (500 mL) and the solution was cooled to −15° C. Diethyl chlorophosphonate (25 mL, 1.74 mol, 1.03 eq) was added, followed by the dropwise addition of 1M LiHMDS in THF (350 mL, 2.07 eq). The LiHMDS was added over 100 minutes while maintaining a reaction temperature between −12° C. and −15° C. The reaction was allowed to warm slowly to RT and aged overnight. The reaction was quenched with water and extracted twice with ether. The ether layer was washed with brine, dried with sodium sulfate, filtered and concentrated to give compound J-2.

Step C

Compound J-2 was dissolved in ethanol (150 mL), 50% NaOH (24 mL) was added and the mixture was refluxed for 5 hours. The reaction was acidified with 12 N HCl (60 mL) at which point it solidified. The mass was diluted with ethanol (50 mL) and methanol (200 mL), and filtered. The cake was washed with ethanol, and the filtrate was concentrated and flushed with isopropyl alcohol (500 mL). Additional isopropyl alcohol was added and the mixture concentrated to circa 300 mL. The slurry was filtered and the resulting cake was washed with isopropyl alcohol. The solid cakes were combined to give compound J-3.

Step D

Compound J-3 was dissolved in methanol (IL) and saturated with HCl gas. The solution was refluxed for 72 hr, then concentrated and partitioned between ether and saturated $NaHCO_3$ solution. The ether layer was dried with $Na_2SO_4$, filtered and concentrated to afford compound J-4. Additional compound J-4 was obtained from the filtrate above by similar treatment with HCl/MeOH followed by chromatography (silica 90/10/1 $CH_2Cl_2$/MeOH/$NH_4OH$).

Step E

Compound J-4 was dissolved in 6N HCl (300 mL) and the solution was refluxed for 3 hr. The solution was then concentrated and the resulting residue was dissolved in water and re-concentrated. The residue was then flushed with isopropyl alcohol (2×300 mL) and ethyl acetate (2×500 mL). The resulting slurry was stirred at room temperature for 1 hr and filtered. The resulting solid was washed with ethyl acetate and dried to give compound J-5.

EXAMPLE 1

Preparation of N-[3-(1-{[(3S,4R)-1-tert-butyl-4-(2,4-difluorophenyl)pyrrolidin-3-yl]carbonyl}piperidin-4-yl)-1,1,5,5-tetramethylhexyl]acetamide (1-1)

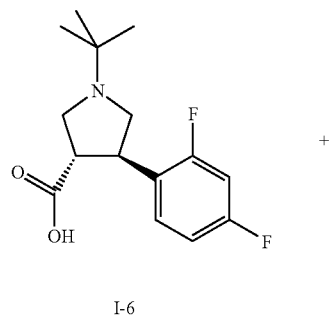

I-6

+

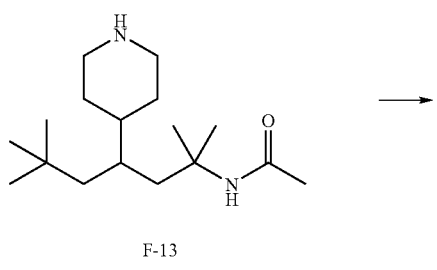

F-13

→

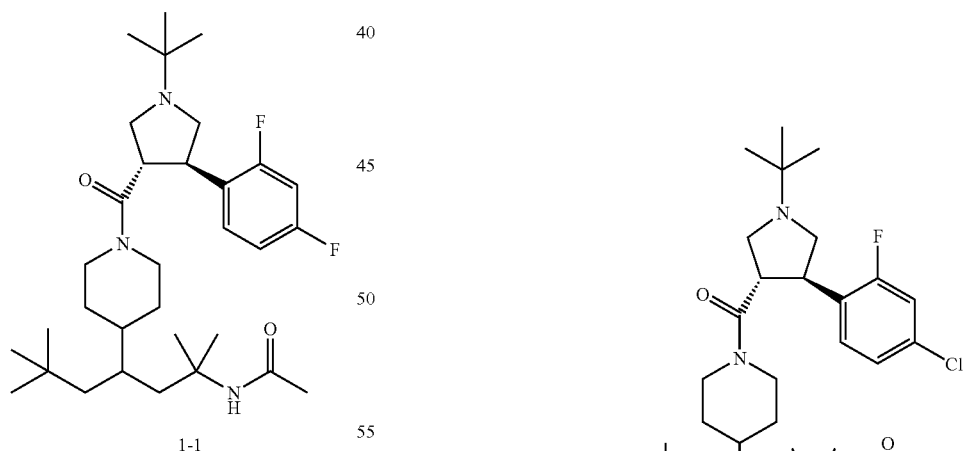

1-1

To a solution of 1-6 (82 mg, 0.29 mmol) in methylene chloride (5 ml) was added EDC (111 mg, 0.58 mmol), HOBT (78 mg, 0.58 mmol), NMM (101.5 mg, 1 mmol) and F-13 (82 mg, 0.29 mmol). After stirring the reaction mixture at room temperature for overnight, mixture was concentrated and purified by preparative tlc using 90:9:1 of methylene chloride:isopropanol: 2N solution of ammonia in methanol to give 1-1. ES-MS: Calcd. For $C_{32}H_{51}F_2N_3O_2$: 547. Found 548 (M$^+$+1).

EXAMPLE 2

Preparation of N-[3-(1-{[(3S,4R)-1-tert-butyl-4-(4-chloro-2-fluorophenyl)pyrrolidin-3-yl]carbonyl}piperidin-4-yl)-1,1,5,5-tetramethylhexyl]acetamide (2-1)

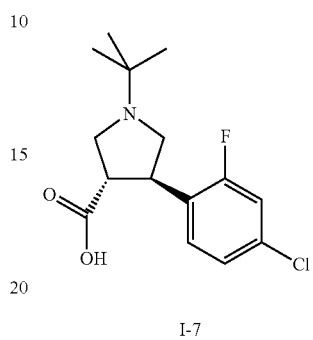

I-7

+

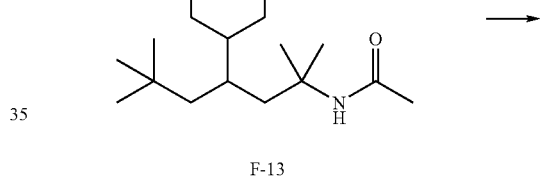

F-13

→

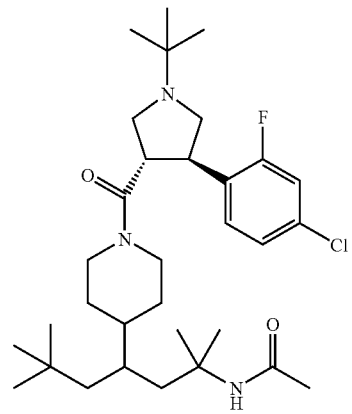

2-1

To a solution of I-7 (86.7 mg, 0.29 mmol) in methylene chloride (5 ml) was added EDC (111 mg, 0.58 mmol), HOBT (78 mg, 0.58 mmol), NMM (101.5 mg, 1 mmol) and F-13 (82 mg, 0.29 mmol). After stirring the reaction mixture overnight at room temperature, the mixture was concentrated and puri-

EXAMPLE 3

Preparation of N-[3-(1-{[(3S,4R)-1-tert-butyl-4-(4-chloro-2-fluorophenyl)pyrrolidin-3-yl]carbonyl}piperidin-4-yl)-1,1,5,5-tetramethylhexyl]-N-methylacetamide (3-4)

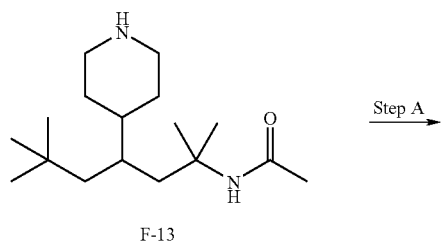

F-13 → Step A

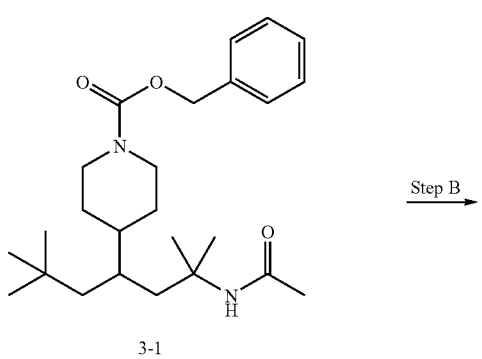

3-1 → Step B

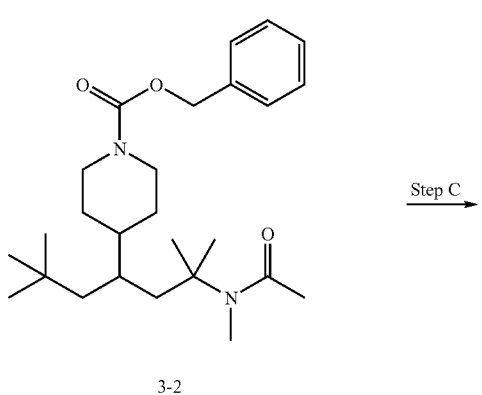

3-2 → Step C

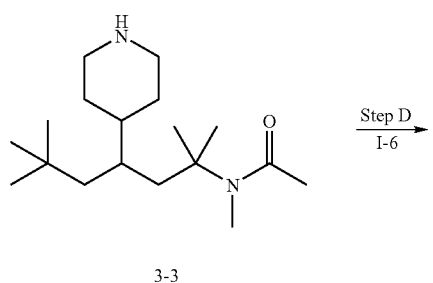

3-3 → Step D, I-6

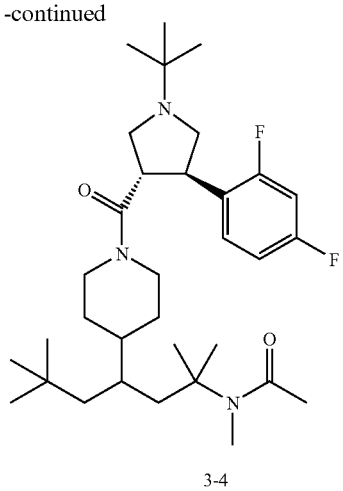

3-4

Step A:

To a solution of F-13 (1.1 g, 3.95 mmol) in methylene chloride (20 ml) was added aqueous sodium carbonate (1.69 g in 10 ml of water) and N-(benzyloxycarbonyloxy)-succinimide (983 mg, 3.95 mmol). After stirring the reaction mixture for overnight at room temperature, the mixture was diluted with methylene chloride and washed with brine. The organic layer was dried, concentrated and purified by chromatography (10% ethyl acetate/methylene chloride) to give 3-1. ES-MS: Calcd. For $C_{25}H_{40}N_2O_3$: 416. Found 417 ($M^+ + 1$).

Step B:

To a solution of 3-1 (308 mg, 0.74 mmol) in DMF (5 ml) was added NaH (71.04 mg, 2.96 mmol). After stirring the reaction mixture at 70° for 1 hr, the mixture was cooled to room temperature and methyl iodide (420 mg, 2.96 mmol) was added. Reaction mixture was stirred for 4 hr at room temperature, then diluted with water and extracted with ethyl acetate. Organic layer was dried, concentrated and purified by preparative tlc (40% ethyl acetate/hexane) to give 3-2. ES-MS: Calcd. For $C_{26}H_{42}N_2O_3$: 430. Found 431 ($M^+ + 1$).

Step C:

To a solution of 3-2 (160 mg) in ethanol was added 10% Pd(OH)$_2$ (25 mg) and 4N HCl in dioxane (0.5 ml). After stirring the reaction mixture for 3 hr under a hydrogen atmosphere, mixture was filtered and concentrated to give 3-3.

Step D:

To a solution of 1-6 (104.7 mg, 0.37 mmol) in methylene chloride (5 Ml) was added EDC (141.85 mg, 0.74 mmol), HOBT (99.9 mg, 0.74 mmol), NMM (150.2 mg, 1.48 mmol) and 3-3 (146 mg, 0.37 mmol). After stirring the reaction for overnight at room temperature, mixture was concentrated and purified by preparative tlc (90:9:1 methylene/isopropanol/2N ammonia in methanol) to give 3-4. ES-MS: Calcd. For $C_{33}H_{53}F_2N_3O_2$: 561. Found 562 ($M^+ + 1$).

EXAMPLE 4

Preparation of N-[3-(1-{[(3S,4R)-1-tert-butyl-4-(2,4-difluorophenyl)pyrrolidin-3-yl]carbonyl}piperidin-4-yl)-3-cyclopentyl-1,1-dimethylpropyl]acetamide (4-1)

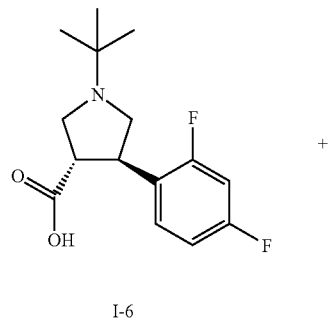

I-6

+

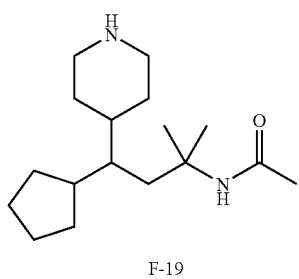

F-19

→

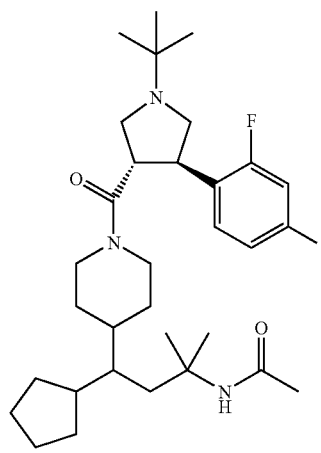

4-1

To a solution of I-6 (227 mg, 0.803 mmol) in methylene chloride (5 ml) was added EDC (231.9 mg, 1.21 mmol), HOBT (122.8 mg, 1.21 mmol), NMM (325.8 mg, 3.2 mmol) and F-19 (254 mg, 0.803 mg). After stirring overnight at room temperature, the reaction mixture was concentrated and purified by preparative tlc to give 4-1. ES-MS: Calcd. For $C_{32}H_{49}F2N_3O_2$:545. Found 546 (M$^+$+1).

EXAMPLE 5

Preparation of N-[3-(1-{[(3S,4R)-1-tert-butyl-4-(4-chloro-2-fluorophenyl)pyrrolidin-3-yl]carbonyl}piperidin-4-yl)-3-cyclopentyl-1,1-dimethylpropyl]acetamide (5-1)

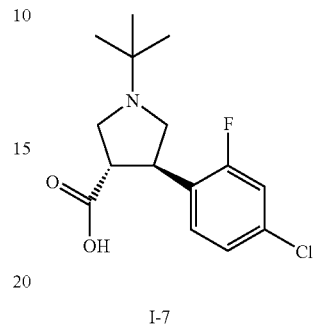

I-7

+

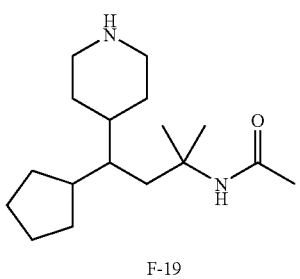

F-19

→

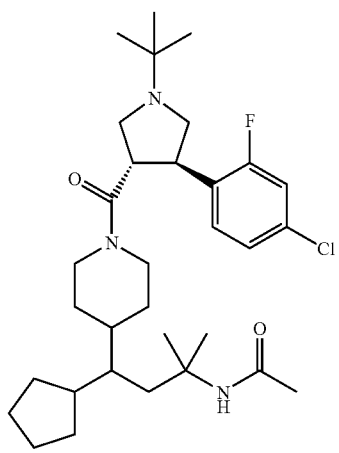

5-1

To a solution of I-7 (66.9 mg, 0.224 mmol) in methylene chloride (5 ml) was added EDC (86 mg, 0.45 mmol), HOBT (60.75 mg, 0.45 mmol), NMM (101.5 mg, 1.0 mmol) and F-19 (71 mg, 0.224 mmol). After stirring overnight at room temperature, the reaction mixture was concentrated and purified by preparative tlc to give 5-1. ES-MS: Calcd. For $C_{32}H_{49}ClFN_3O_2$: 561. Found 562 (M$^+$+1).

EXAMPLE 6

Preparation of N-[3-(1-{[(3R,4R)-1-tert-butyl-3-(2,4-difluorophenyl)piperidin-4-yl]carbonyl}piperidin-4-yl)-3-cyclopentyl-1,1-dimethylpropyl]acetamide (6-1)

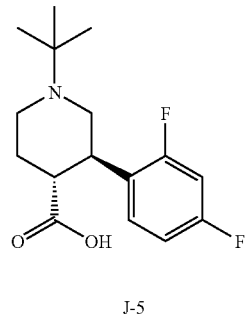

J-5

+

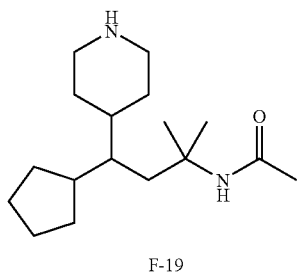

F-19

→

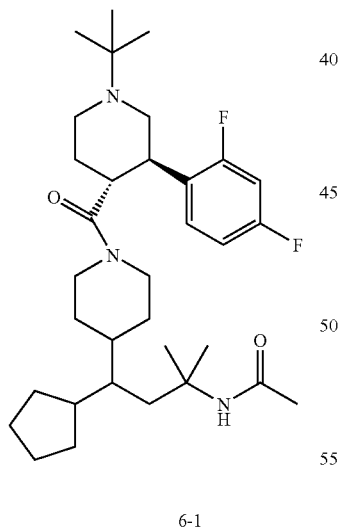

6-1

To a solution of J-5 (49.59 mg, 0.167 mmol) in methylene chloride (5 ml) was added HATU (126.9 mg, 0.334 mmol), HOAT (22.7 mg, 0.167 mmol), DIEA (86.17 mg, 0.668 mmol) and F-19 (53 mg, 0.167 mmol). After stirring overnight at room temperature, the reaction mixture was concentrated and purified by preparative tlc (91:9: 1, $CH_2Cl_2$/EPA/ 2M $NH_3$ in methanol) to give 6-1. ES-MS: calcd. For $C_{33}H_{51}F_2N_3O_2$: 559. Found 560 ($M^+$+1).

EXAMPLE 7

Preparation of N-[3-(1-{[(3S,4R)-1-tert-butyl-4-(2,4-difluorophenyl)pyrrolidin-3-yl]carbonyl}piperidin-4-yl)-3-cyclopentyl-1,1-dimethylpropyl]-N-methylacetamide (7-4)

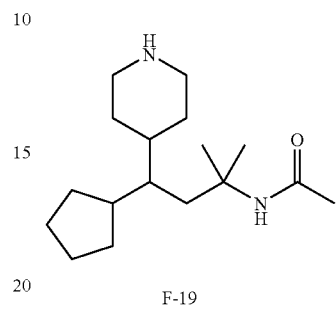

F-19

Step A →

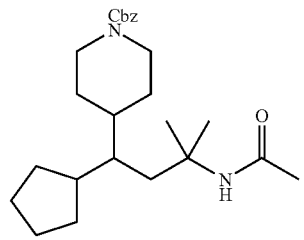

7-1

Step B →

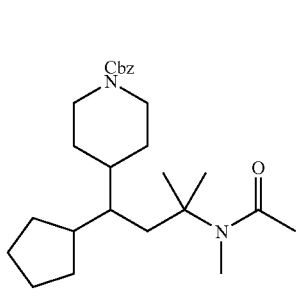

7-2

Step C →

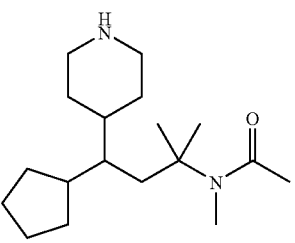

7-3

Step D I-6 →

-continued

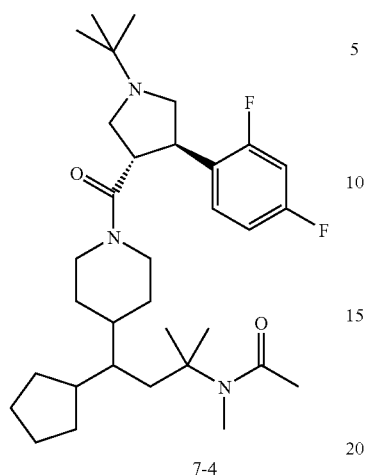

7-4

Step A:

To a solution of F-19 (568 mg, 2.03 mmol) in methylene chloride (10 ml) was added N-(benzyloxycarbonyloxy)-succinimide (522.9 mg, 2.1 mmol) and triethylamine (303.5 mg, 3 mmol). After stirring the reaction mixture for overnight at room temperature, mixture was concentrated and purified by preparative tlc (10% EtOAc/CH$_2$Cl$_2$) to give 7-1. ES-MS: Calcd. For C$_{25}$H$_{38}$N$_2$O$_3$: 414. Found 415 (M$^+$+1).

Step B:

To a solution of 7-1 (700 mg, 1.69 mmol) in DMF (8 ml) was added NaH (243 mg, 10.1 mmol) and imidazole (20 mg). After stirring the reaction mixture at 70° for 1 hr, mixture was cooled to room temperature and methyl iodide (1.439 g, 10.14 mmol) was added. Mixture was further stirred for 2 hr, diluted with water and extracted with ethyl acetate. Organic layer was dried, concentrated and purified by preparative tlc (30% ethyl acetate/hexane) to give 7-2. ES-MS: Calcd. For C$_{26}$H$_{40}$N$_2$O$_3$: 428. Found 429 (M$^+$+1).

Step C:

To a solution of 7-2 (303 mg) in ethanol was added 10% Pd(OH)$_2$ (30 mg) and 4N HCl in dioxane (0.2 ml). After stirring for 3 hr under hydrogen atmosphere, the reaction mixture was filtered and concentrated to give 7-3. ES-MS: Calcd. For C$_{18}$H$_{34}$N$_2$O: 294. Found 295 (M$^+$+1).

Step D:

To a solution of 1-6 (110 mg, 0.354 mmol) in methylene chloride (5 ml) was added EDC (134.9 mg, 0.704 mmol), HOBT (95 mg, 0.704 mmol), NMM (143 mg, 1.41 mmol) and 7-3 (117 mg, 0.354 mmol). After stirring overnight at room temperature, the reaction mixture was concentrated and purified by preparative tlc to give 7-4. ES-MS: Calcd. For C$_{33}$H$_{51}$F$_2$N$_3$O$_2$: 559. Found 560 (M$^+$+1).

EXAMPLE 8

Preparation of N-{1-[(2S)-2-(1-{[(3S,4R)-1-tert-butyl-4-(2,4-difluorophenyl)pyrrolidin-3-yl]carbonyl}piperidin-4-yl)-2-cyclopentylethyl]cyclopropyl}-1-N-methylacetamide (8-1)

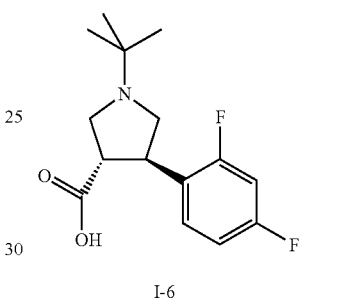

I-6

+

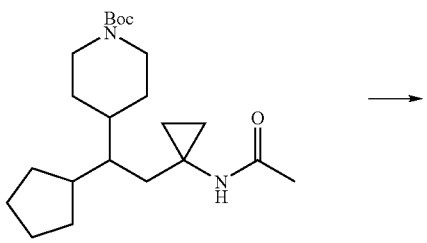

G-8a

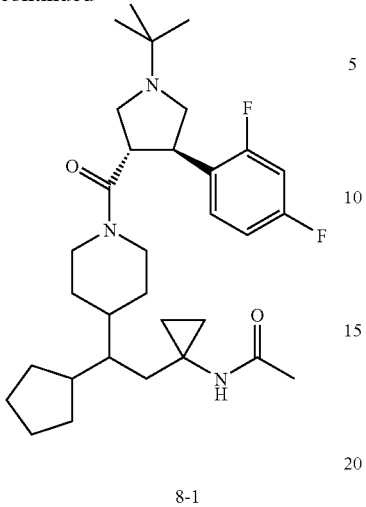

8-1

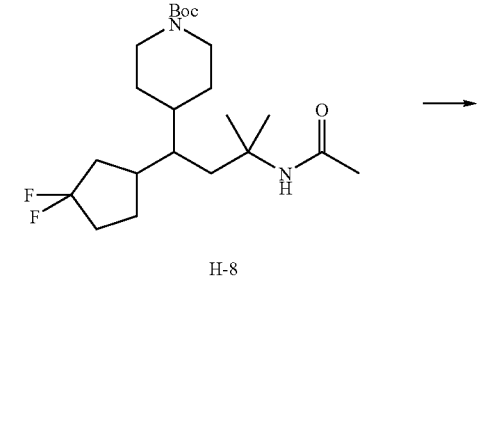

H-8

4M HCl in dioxane (3.0 mL) was added to a solution of BOC acetamide G-8a (82 mg, 0.21 mmol) in dichloromethane (2 mL) and stirred at ambient temperature for 1 h. The solvent was evaporated and the residue was triturated with ether stirring for 15 min. The ether was decanted, the white solid residue was dried briefly under vacuum and then dissolved in dichloromethane (3 mL) with N,N-diisopropylethylamine (56 μL, 0.32 mmol). The resulting solution was then added to a stirring solution of 1-6 (3S,4R)-1-tert-butyl-4-(2,4-difluorophenyl) pyrrolidine-3-carboxylic acid (72 mg, 0.26 mmol), 1-hyroxybenzotriazole hydrate (39 mg, 0.26 mmol) and EDC (61 mg, 0.32 mmol) in dichloromethane (3.0 mL). The reaction mixture was stirred overnight at ambient temperature, diluted with dichloromethane, and washed with water, saturated aqueous NaHCO$_3$ and brine, dried over MgSO$_4$, filtered and evaporated. The resulting crude product was purified by preparative TLC (silica gel, 20×20 cm plate, 1000μ thickness with 10% isopropanol-dichloromethane-1% 2M ammonia in methanol) to give 8-1 as a colorless oil. ES-MS: Calculated for $C_{33}H_{49}F_2N_3O_2$: 557.8. Found: [M+H]$^+$=558.7.

EXAMPLE 9

Preparation of N-[3-(1-{[(3S,4R)-1-tert-butyl-4-(2,4-difluorophenyl)pyrrolidin-3-yl]carbonyl}piperidin-4-yl)-3-(3,3-difluorocyclopentyl)-1,1-dimethylpropyl]acetamide (9-1)

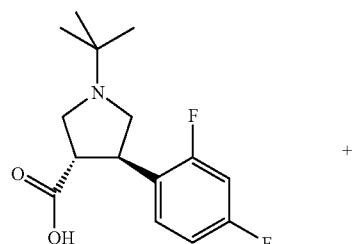

I-6

+

9-1

4M HCl in dioxane (3.0 mL) was added to a solution of BOC acetamide H-8 (132 mg, 0.32 mmol) in dichloromethane (2.01 mL) and stirred at ambient temperature for 1 h. An oil separated which crystallized. The solvent was evaporated and the residue was triturated with ether stirring for 10 min. The ether was decanted, the white solid residue was dried briefly under vacuum (89 mg, 0.25 mmol) and then dissolved in dichloromethane (3.0 mL) with N,N-diisopropylethylamine (44 μL, 0.25 mmol). This solution was then added to a stirring solution of 1-6 (3S,4R)-1-tert-butyl-4-(2,4-difluorophenyl)pyrrolidine-3-carboxylic acid (86 mg, 0.30 mmol), 1-hyroxybenzotriazole hydrate (46 mg, 0.30 mmol) and EDC (73 mg, 0.38 mmol) in dichloromethane (3.0 mL). The reaction mixture was stirred overnight at ambient temperature, diluted with dichloromethane, and washed with water, saturated aqueous NaHCO$_3$ and brine, dried over MgSO$_4$, filtered and evaporated. The crude product was purified by preparative TLC (silica gel, 20×20 cm plate, 1000 u thickness with 10% isopropanol/dichloromethane-1% 2M ammonia in methanol) to give 9-1 as a viscous colorless oil. ES-MS: Calculated for $C_{32}H_{47}F_4N_3O_2$: 581.8. Found: [M+H]$^+$=582.5.

Following compounds were prepared following synthetic route described above and using the appropriate reagents:
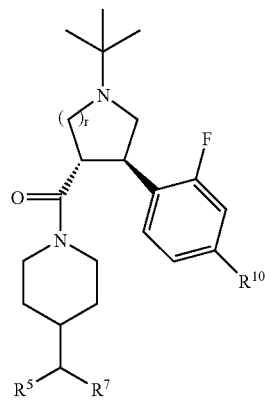
| No. | n | R10 | R5 | R7 | Parent ion $(M + H)^+$ |
|---|---|---|---|---|---|
| 10 | 1 | F | iBuCH2 | -H2C-C(CH3)2-NH-C(O)CH3 | 534 |
| 11 | 1 | F | iBuCH2 | -H2C-C(CH3)2-OH | 493 |
| 12 | 1 | F | cyclohexyl | -H2C-C(CH3)2-NH-C(O)CH3 | 560 |
| 13 | 1 | F | phenyl | -H2C-C(CH3)2-NH-C(O)CH3 | 554 |
| 14 | 1 | F | cyclohexyl | -H2C-C(O)-N(Et)2 | 560 |
| 15 | 1 | F | cyclohexyl | -H2C-N(iPr)-C(O)CH3 | 560 |
| 16 | 1 | F | iPr-CH | -H2C-C(CH3)2-NH-C(O)CH3 | 520 |
| 17 | 1 | F | CF3 | -H2C-C(CH3)2-NH-C(O)CH3 | 546 |

-continued
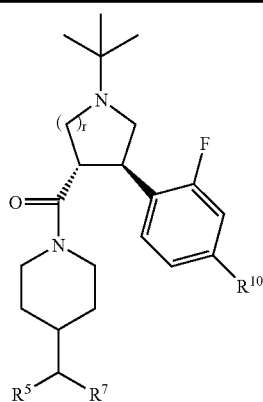
| No. | n | R10 | R5 | R7 | Parent ion (M + H)+ |
|---|---|---|---|---|---|
| 18 | 1 | F | cyclobutyl | -H2C-C(CH3)2-NH-C(O)CH3 | 532 |
| 19 | 1 | F | pentan-3-yl | -H2C-C(CH3)2-NH-C(O)CH3 | 548 |
| 20 | 1 | F | pentan-3-yl | -H2C-C(CH3)2-N(CH3)-C(O)CH3 | 562 |
| 21 | 1 | F | neopentyl (-CH2-C(CH3)3) | -H2C-C(CH3)2-CN | 516 |
| 22 | 1 | Cl | neopentyl (-CH2-C(CH3)3) | -H2C-C(CH3)2-CN | 532 |
| 23 | 1 | F | 4-methylcyclohexyl D1 | -H2C-C(CH3)2-NH-C(O)CH3 | 574 |
| 24 | 1 | F | 4-methylcyclohexyl D2 | -H2C-C(CH3)2-NH-C(O)CH3 | 574 |
| 25 | 1 | F | isobutyl | -H2C-(1-cyclopropyl)-NH-C(O)CH3 | 532 |

-continued
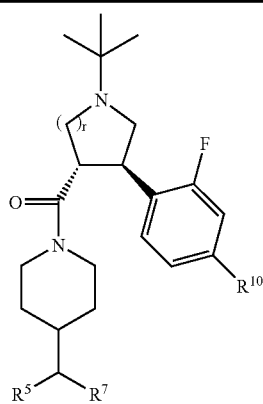
| No. | n | R10 | R5 | R7 | Parent ion (M + H)+ |
|---|---|---|---|---|---|
| 26 | 1 | F | iBuCH2 | H2C-C(cyclopropyl)(NHSO2CH3) | 568 |
| 27 | 1 | F | iBuCH2 | H2C-C(cyclopropyl)(NHC(O)-pyridazin-3-yl) | 596.8 |
| 28 | 1 | F | iBuCH2 | H2C-C(cyclopropyl)(NHC(O)NHEt) | 561.8 |
| 29 | 1 | F | iBuCH2 | H2C-(5-methyl-1,3,4-oxadiazol-2-yl) | 517.8 |
| 30 | 1 | F | iBuCH2 | H2C-(5-isopropyl-1,3,4-oxadiazol-2-yl) | 545.8 |
| 31 | 1 | F | cyclopentyl | H2C-(1-methyl-1,2,4-triazol-5-yl) | 528.6 |
| 32 | 1 | F | cyclopentyl | H2C-(1-isopropyl-1,2,4-triazol-5-yl) | 556.7 |
| 33 | 1 | F | cyclopentyl | H2C-(1-methyl-tetrazol-5-yl) | 529 |

-continued

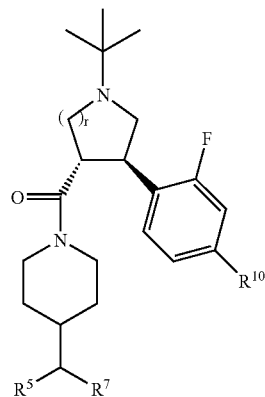

| No. | n | R10 | R5 | R7 | Parent ion (M + H)+ |
|---|---|---|---|---|---|
| 34 | 1 | F | cyclopentyl | —H₂C—N(tetrazole)-ethyl | 543 |
| 35 | 1 | F | cyclopentyl | —H₂C—(tetrazole)N-ethyl | 543 |

Biological Assays

A. Binding Assay.

The membrane binding assay was used to identify competitive inhibitors of $^{125}$I-NDP-alpha-MSH ([Nle4, D-Phe7]-alpha-Melanocyte stimulating hormone) binding to cloned human MCRs expressed in mouse L- or Chinese hamster ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BR1); 100 ml 10% heat-inactivated fetal bovine serum (Sigma); 10 mL 10,000 unit/mL penicillin & 10,000 μg/mL streptomycin (Gibco/BR1); 10 ml 200 mM L-glutamine (Gibco/BR1); 1 mg/mL geneticin (G418) (Gibco/BR1). The cells were grown at 37° C. with CO₂ and humidity control until the desired cell density and cell number was obtained.

The medium was poured off and 10 mls/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min.

The supernatant was discarded and the cells were resuspended in 5 mls/monolayer membrane preparation buffer having the composition: 10 mM Tris pH 7.2-7.4; 4 μg/mL Leupeptin (Sigma); 10 μM Phosphoramidon (Boehringer Mannheim); 40 μg/mL Bacitracin (Sigma); 5 μg/mL Aprotinin (Sigma); 10 mM Pefabloc (Boebringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mls/monolayer membrane prep buffer and aliquots were placed in tubes (500-1000 μL/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM CaCl₂; 1 mM MgCl₂; 5 mM KCl; 0.2% BSA; 4 μg/mL Leupeptin (SIGMA); 10 μM Phosphoramidon (Boehringer Mannheim); 40 μg/mL Bacitracin (SIGMA); 5 μg/mL Aprotinin (SIGMA); and 10 mM Pefabloc (Boehringer Mannheim). One hundred μL of membrane binding buffer containing 10-40 μg membrane protein was added, followed by 100 μM 125I-NDP-α-MSH to final concentration of 100 pM. The resulting mixture was vortexed briefly and incubated for 90-120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 mL per well) with room temperature of filter wash having the composition: 50 mM Tris-HCl pH 7.2 and 20 mM NaCl. The filter was dried, and the bottom sealed and 50 μL of Packard Microscint-20 was added to each well. The top was sealed and the radioactivity quantitated in a Packard Topcount Microplate Scintillation counter.

Representative compounds of the present invention were tested and found to bind to the melanocortin-4 receptor. These compounds were generally found to have $IC_{50}$ values less than 10 μM.

B. Functional assay.

Functional cell based assays were developed to discriminate melanocortin receptor agonists from antagonists.

Cells (for example, CHO— or L-cells or other eukaryotic cells) expressing a human melanocortin receptor (see e.g. Yang-Y K; Ollmann-M M; Wilson-B D; Dickinson-C; Yamada-T; Barsh-G S; Gantz-I; Mol-Endocrinol. 1997 March; 11(3): 274-80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to $5 \times 10^6$/mL. The phosphodiesterase inhibitor 3-isobutyl-1-methylxanthine was added to cells to 0.6 mM.

Test compounds were diluted in DMSO ($10^{-5}$ to $10^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min, and an $EC_{50}$ dose (approximately 10 nM alpha-MSH) was added to the cells. The assay was terminated at 45 min and cAMP quantitated as above. Percent inhibition was determined by comparing the amount of cAMP produced in the presence to that produced in the absence of test compound.

Representative compounds of the present invention were also tested in the functional assay and found generally to activate the melanocortin-4 receptor with $EC_{50}$ values less than 10 μM.

C. In vivo food intake and body weight models.

1) Food intake and body weight in rats. Sprague Dawley rats are administered test compound one hour prior to onset of dark cycle (12 hours). Food intake is determined either by measurement of the remaining amount of preweighed food the morning following the dosing or by using a computerized system in which each rat's food is placed on a computer monitored balance. Cumulative food intake for 16 h post compound administration is measured. In some cases, food intake measurements are followed as long as 2 weeks. Body weight is measured daily; in some cases, adiposity is measured by DEXAscan analysis, tissue weights and plasma drug levels are measured. Animals can be dosed by a number of routes of administration. The routes of administration include intravenous (IV), intraperitoneal (IP), subcutaneous (SC) and intracerebral ventricular (ICV).

Compounds useful in the present invention decrease food intake acutely by at least 20% and/or decrease body weight in a 2 week period by at least 4% relative to placebo.

2) Food intake in diet induced obese mice. Male C57/B16J mice maintained on a high fat diet (30-60% fat calories) are dosed with test compound for 1 to 30 days. Food intake and body weight are measured overnight and sometimes daily as long as 30 days. Biochemical parameters relating to obesity, including leptin, insulin, triglyceride, free fatty acid, cholesterol and serum glucose levels and pharmacokinetic parameters may be determined. Animals can be dosed by a number of routes of administration. The routes of administration include intravenous (IV), intraperitoneal (IP), subcutaneous (SC) and intracerebral ventricular (ICV).

Compounds useful in the present invention decrease body weight by at least 4% relative to placebo.

D. Male Sexual Dysfunction: Mouse electrically stimulated cavernosal nerve (ESCN) assay Male C57BL6 mice are anesthetized, the carotid artery is exposed and cannulated for measurement of arterial pressure (MAP). A 30G needle attached to PE10 tubing, filled with heparinized saline, was inserted into the artery and glued in place. This tubing was connected to a pressure transducer and amplifier to measure direct MAP on a Gould 8 channel oscilloscope connected to a computer using the Po-ne-mah software to collect the data at one minute intervals. Another PE10 line attached to a 30G needle was inserted into the jugular vein for compound or vehicle administration. The cavernous nerve and penile body were exposed through a midline incision. Surrounding muscles were cauterized and removed for visualization of the cavernous nerve, which arises from the ipsilateral pelvic ganglion and is situated dorsal to the prostate. Another 30G needle attached to PE10 tubing, filled with heparinized saline, was inserted into the base of the corpus cavernosum near the crura and connected to the Gould system. A slight increase in intercavernous pressure (ICP) of approximately 5 to 10 mmHg is observed once this cannula is inserted into the corpus cavernosum. Heparinized saline (200 units/mL) was flushed through the cannula to assure proper placement of the cannula, inducing tumescence. The cavernous nerve was then isolated using curved #5 Dumont forceps and placed on a modified fixed position bipolar silver electrode (Harvard Apparatus). The electrodes are encased in plastic to allow stimulation of the nerve without additional stimulation of surrounding tissues. The electrode was advanced and held by a micromanipulator and was attached to a square wave stimulator to deliver electrical impulses at stimulation parameters ranging between 0.5 to 6.0v, 2 to 16 Hz, 1 ms, for 30 seconds. Electrical stimulations were administered to individual animals with 5 minute intervals between stimulations. Responses reported at each time point represent the mean of the two stimulations. ICP, MAP and ICP/MAP responses were continuously recorded at one second intervals for the duration of the experiment.

Measurements of ICP, MAP and ICP/MAP ratio are analyzed and responses compared to nerve stimulation in the presence and absence of compound or vehicle. For each parameter monitored, responses evoked by duplicate electrical stimulations were averaged, and the mean values were used for comparison. Response segments of 10 s of baseline +30 s stimulation +150 s post-stimulation were used to evaluate changes in ICP in response to electrical stimulation of the cavernous nerve. To assess direct effects of compound administration on ICP, a 300 s pre-compound response segment was compared to a comparable segment immediately after compound administration.

Compounds useful in the present invention increase intracavernous pressure by at least 25% for a time period of at least 15 minutes relative to placebo.

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276-R1285, 1991; McKenna K E et al, *Modulation By Peripheral Serotonin of The Threshold For Sexual Reflexes In Female Rats*, Pharm. Bioch. Behav., 40:151-156, 1991; and Takahashi L K et al, *Dual Estradiol Action In The Diencephalon And The Regulation Of Sociosexual Behavior In Female Golden Hamsters*, Brain Res., 359:194-207, 1985.

EXAMPLES OF PHARMACEUTICAL COMPOSITIONS

As a specific embodiment of an oral composition of a composition of the present invention, 5 mg of Example 3 is formulated with sufficient finely divided lactose to provide a total amount of 580 to 1000 mg to fill a size O hard gelatin capsule.

As another specific embodiment of an oral composition of a compound of the present invention, 2.5 mg of Example 4 is formulated with sufficient finely divided lactose to provide a total amount of 580 to 1000 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound selected from the group consisting of:

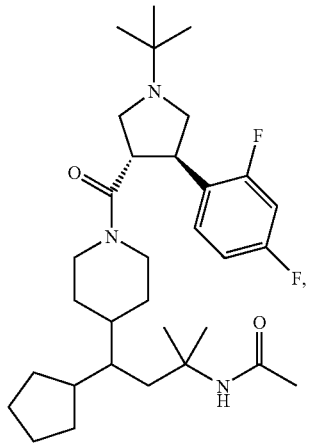

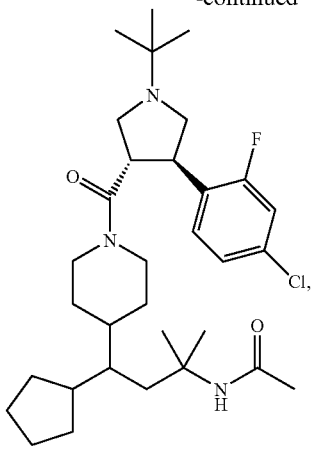

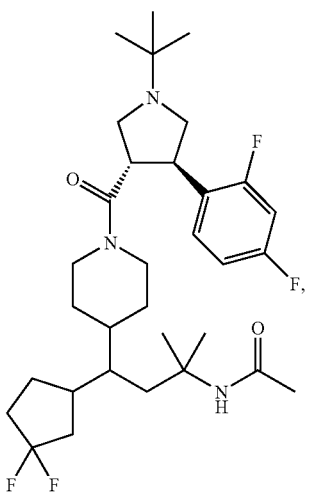

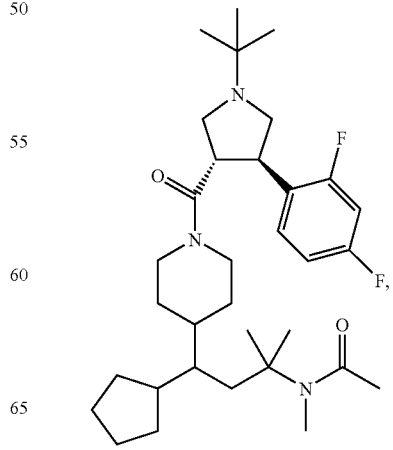

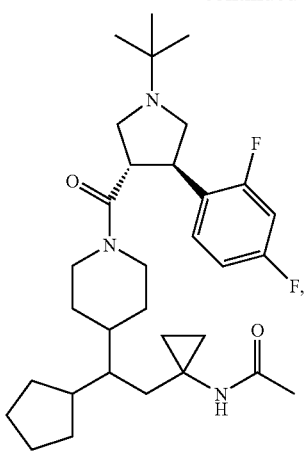

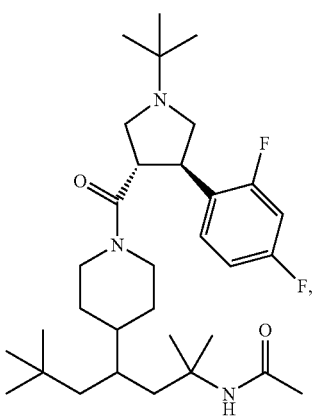

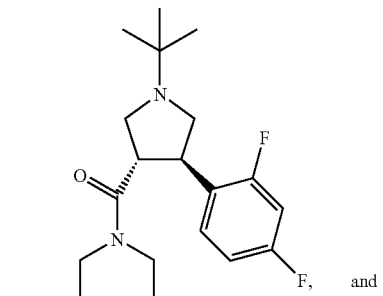

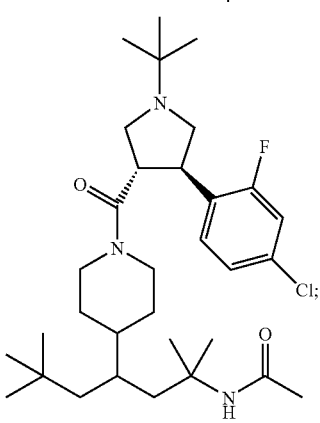

and

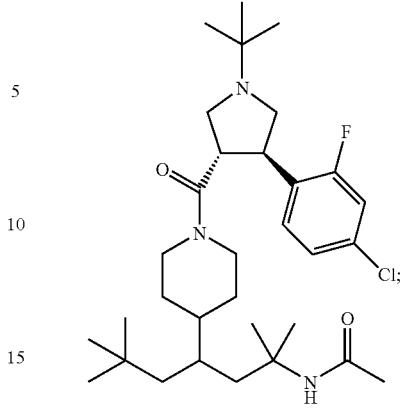

or a pharmaceutically acceptable salt thereof.

2. The compound of claim 1 which is:

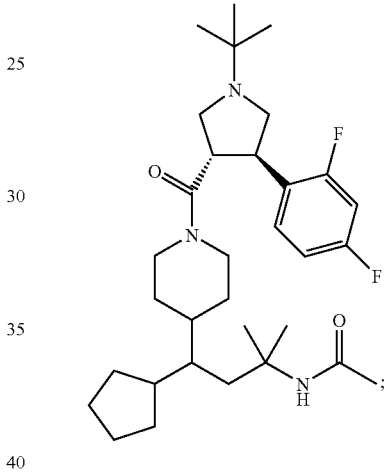

or a pharmaceutically acceptable salt thereof.

3. The compound of claim 1 which is:

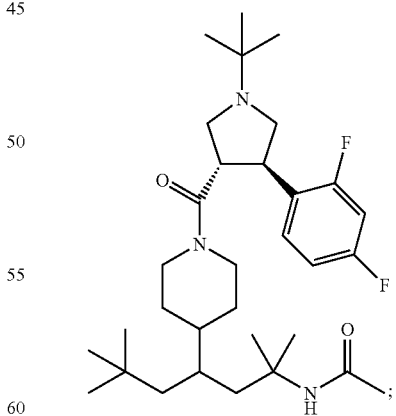

or a pharmaceutically acceptable salt thereof.

4. A pharmaceutical composition which comprises a compound of claim 1 and a pharmaceutically acceptable carrier.

5. The compound of claim 1 wherein the pharmaceutically acceptable salt is the hydrochloride salt.

6. A compound selected from the group consisting of:
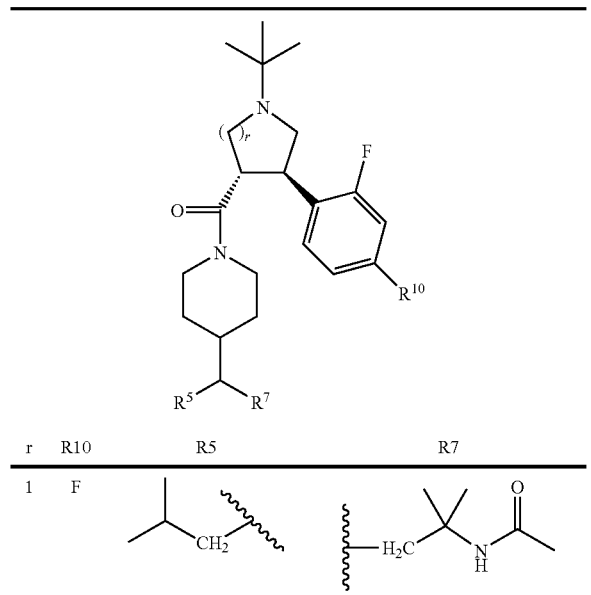
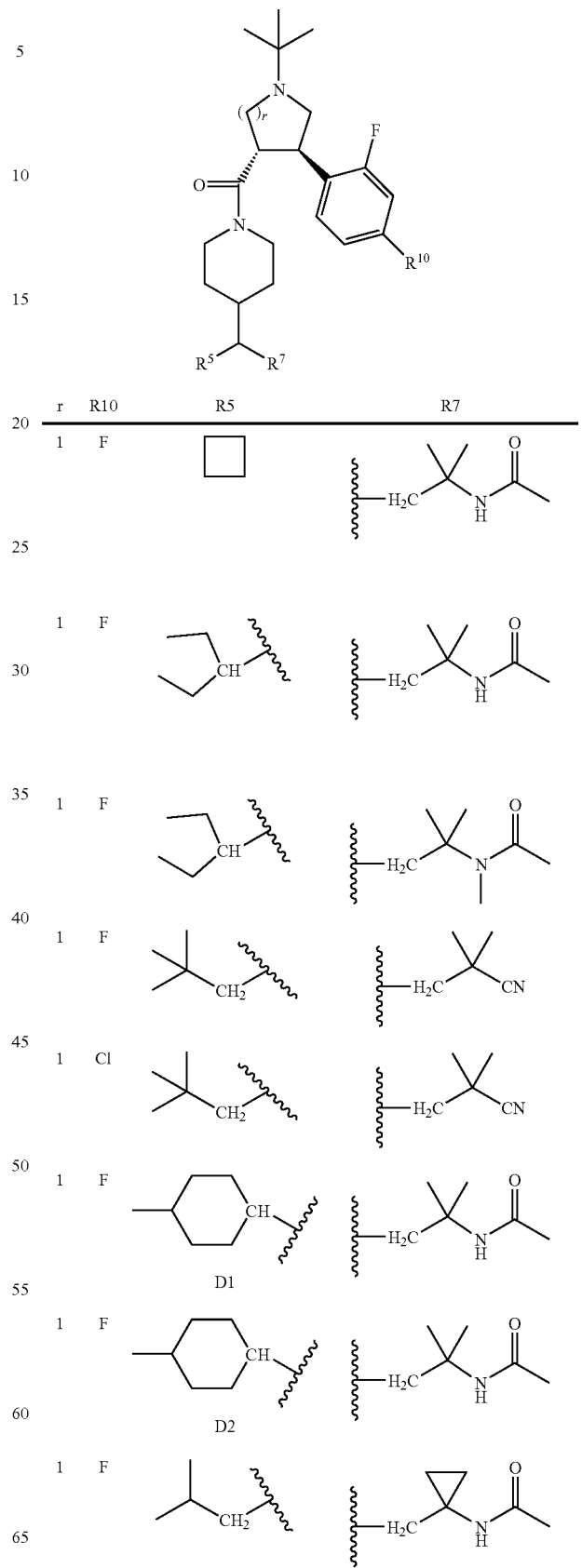

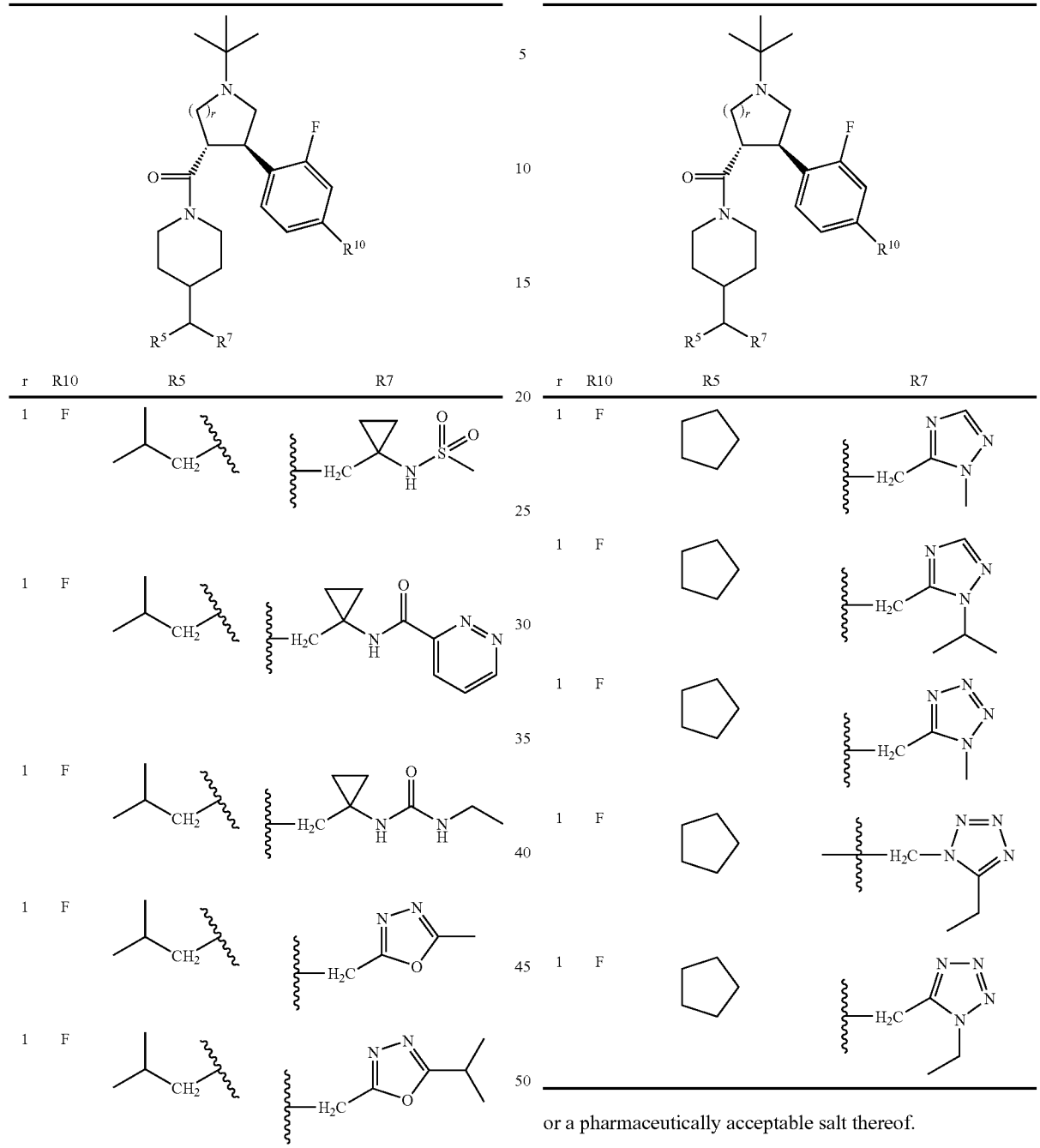
or a pharmaceutically acceptable salt thereof.
* * * * *